(12) United States Patent
Gilbert

(10) Patent No.: US 7,992,270 B2
(45) Date of Patent: Aug. 9, 2011

(54) SINGLE STAGE TAMPON MOLDING

(75) Inventor: Steven Ray Gilbert, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 719 days.

(21) Appl. No.: 11/860,614

(22) Filed: Sep. 25, 2007

(65) Prior Publication Data

US 2009/0082748 A1 Mar. 26, 2009

(51) Int. Cl.
*A61F 13/20* (2006.01)
(52) U.S. Cl. .......................................................... 28/118
(58) Field of Classification Search .................... 28/118, 28/119, 120, 122, 123, 116; 264/319, 324, 264/320, 325; 604/385.17, 904
See application file for complete search history.

(56) References Cited

U.S. PATENT DOCUMENTS

| | | | | |
|---|---|---|---|---|
| 4,109,354 A | * | 8/1978 | Ronc | 28/119 |
| 4,951,368 A | * | 8/1990 | Heinen | 28/118 |
| 5,634,248 A | * | 6/1997 | McNelis et al. | 28/118 |
| 6,003,216 A | * | 12/1999 | Hull et al. | 28/119 |
| 6,824,536 B2 | | 11/2004 | Randall et al. | |
| 6,932,805 B2 | | 8/2005 | Kollwitz et al. | |
| 7,047,608 B2 | * | 5/2006 | Sageser et al. | 28/118 |
| 7,120,977 B2 | | 10/2006 | Bittner et al. | |
| 7,124,483 B2 | | 10/2006 | Prosise et al. | |
| 7,472,463 B2 | | 1/2009 | Gilbert et al. | |
| 7,735,203 B2 | * | 6/2010 | Stan et al. | 28/118 |
| 7,736,572 B2 | * | 6/2010 | Gilbert et al. | 264/320 |
| 2004/0244165 A1 | * | 12/2004 | Bittner et al. | 28/118 |
| 2005/0027275 A1 | | 2/2005 | Wasson et al. | |
| 2008/0119811 A1 | * | 5/2008 | Gilbert et al. | 604/385.17 |

OTHER PUBLICATIONS

PCT International Search Report dated Feb. 19, 2009.
U.S. Appl. No. 11/799,914, filed May 3, 2007, Gilbert et al.
U.S. Appl. No. 11/601,946, filed Nov. 20, 2006, Gilbert et al.
U.S. Appl. No. 11/504,983, filed Aug. 16, 2006, Gilbert et al.
U.S. Appl. No. 11/595,322, filed Nov. 10, 2006, Gilbert et al.
U.S. Appl. No. 11/860,655, filed Sep. 25, 2007, Hasse et al.

* cited by examiner

*Primary Examiner* — Amy B Vanatta
(74) *Attorney, Agent, or Firm* — Andrew J. Hagerty; David M. Weirich

(57) ABSTRACT

A method for making a tampon including providing a tampon pledget, and providing a compression/stabilization mold. The method includes moving the tampon pledget into the compression/stabilization mold via a transfer member, wherein the compression/stabilization mold is in an open position, and laterally compressing the tampon pledget in the compression/stabilization mold by closing the compression/stabilization mold to form a stabilized tampon. An apparatus for making a tampon and a tampon made by the method are also disclosed.

11 Claims, 21 Drawing Sheets

SINGLE STAGE TAMPON MOLDING

FIELD OF THE INVENTION

The invention relates to improved tampons and to apparatuses and methods of making such tampons.

BACKGROUND OF THE INVENTION

Tampons are generally compressed absorbent structures typically shaped and sized to fit into a body cavity, such as, for example a human vagina. In conventional processes used for making tampons, relatively high drag forces may exist when loading certain types of molds. When some types of molds are axially loaded, relatively wide density profiles may be created along the length of a tampon product, such that a suitable tampon product may not be formed. For example, in a conventional two-stage molding process, a pledget or uncompressed fibrous material may initially be compressed in a lateral dimension via a crossdie compression step. This stage may form the uncompressed material into a cylindrical shape or cylinder of fibrous material. A subsequent stage may compress the cylinder of fibrous material in an axial dimension by pushing the cylinder into a cylindrically-shaped mold or cavity. This stage may create relatively high drag forces on the cylinder thus causing the relatively wide density profiles along the length of the tampon product.

In certain tampon types, for instance, shaped tampons with surface textures, e.g., flutes, petals or impressed patterns, the relatively high drag forces may hinder the formation of a suitable tampon product with the desired surface smoothness, shape and texturing. In these instances, the high drag forces may create imperfections in the surface smoothness, shape and/or texturing.

Often times, when shaped and textured tampons are removed from conventional molds, product removal may be difficult if the mold does not open or otherwise fails to release the product. In these instances, the manufacturing process may be delayed and additional time and expense may be incurred to open the mold and/or release the product from the mold.

Yet other certain tampon types may utilize the impact of fins or other features to mold a suitable tampon product with the desired shape and texturing. In these instances, the impact may create inconsistencies or irregularities in the density profile of the tampon.

Accordingly, it may be desirable to reduce or eliminate any high drag forces on the fibrous material during tampon production. Furthermore, it may be advantageous to have a system and/or apparatus that can combine manufacturing elements or actions to improve manufacturing efficiency and capacity. In addition, it may be advantageous to have molds with improved opening and release capabilities. Moreover, it may be desirable to reduce or eliminate inconsistencies or irregularities in the density profile of the tampon. Further still, it would be desirable to provide an apparatus and/or method of making a tampon that reduces or eliminates the high drag forces and/or inconsistencies or irregularities in the density profile of the tampon during tampon production and/or provide a mold with improved opening and release capabilities.

SUMMARY OF THE INVENTION

Embodiments of the invention address one or more of the foregoing technical problems and provide a method for producing a stabilized tampon from a tampon pledget. The method may include providing a tampon pledget, providing a compression/stabilization mold, moving the tampon pledget into the compression/stabilization mold via a transfer member, wherein the compression/stabilization mold is in an open position, and laterally compressing the tampon pledget in the compression/stabilization mold by closing the compression/stabilization mold to form a stabilized tampon.

According to another aspect of this invention, an apparatus for compressing a tampon pledget may include a compression/stabilization mold capable of receiving a tampon pledget when the compression/stabilization mold is in an open position, and a force application member capable of laterally compressing the tampon pledget when the compression/stabilization mold is closed, wherein the compression/stabilization mold can form a stabilized tampon.

According to another aspect of this invention, a tampon may be provided that is made in accordance with the method described above.

Other features and advantages of the invention may be apparent from reading the following detailed description, drawings, and claims.

DETAILED DESCRIPTION OF THE INVENTION

Figure 1:
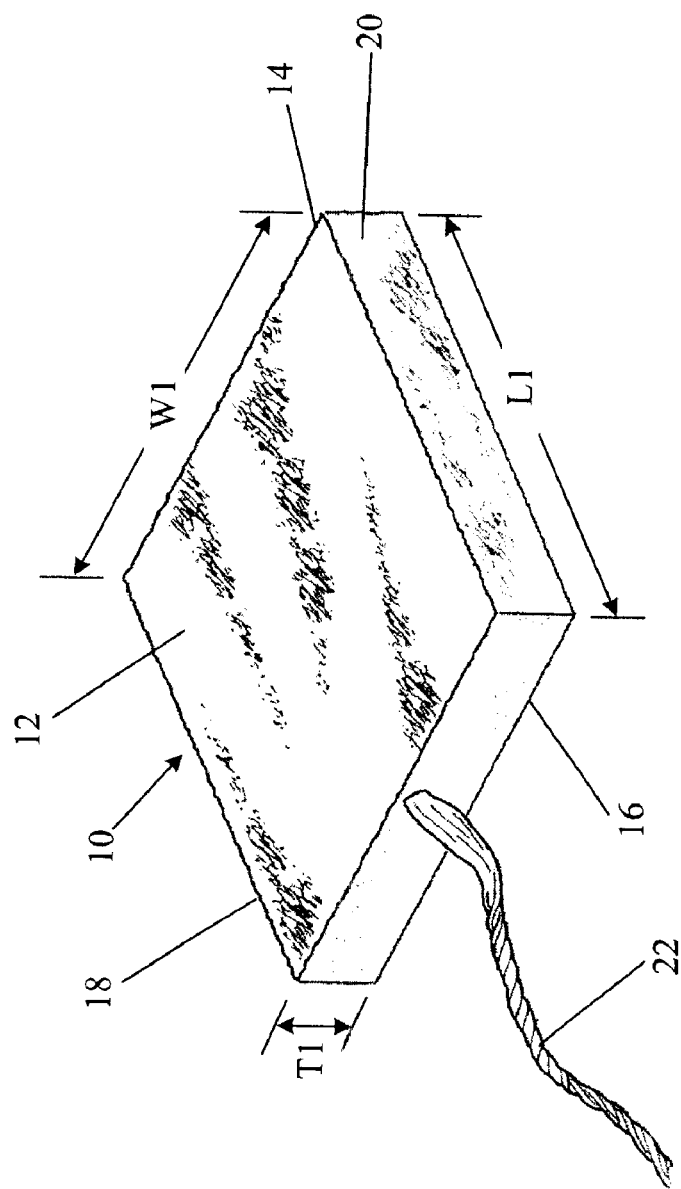
FIG. 1 is a perspective view of an uncompressed pledget of absorbent material for use in making a tampon in accordance with an embodiment of the invention.
Figure 2:
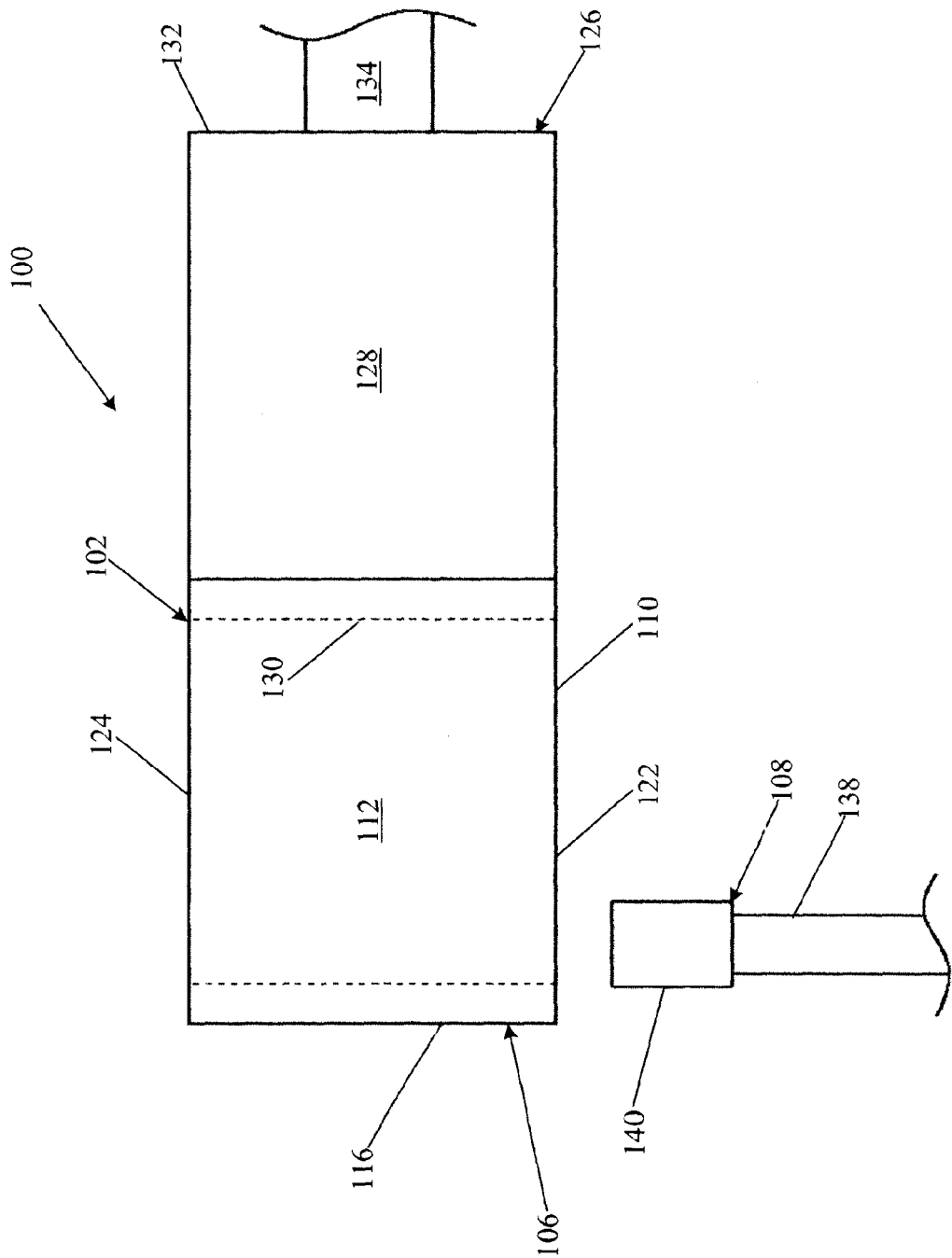
FIG. 2 is a plan view of a tampon forming apparatus, in accordance with an embodiment of the invention, with the tampon compression crossdie in an open position.

As summarized above, an embodiment of the invention may encompass a tampon and an apparatus and method for making such a tampon. As will be explained in more detail below, tampons in accordance with embodiments of the invention may be made by compressing an uncompressed tampon pledget of absorbent material with a tampon forming apparatus which may have a single combined compression and conditioning stage to produce a desired shape and texturing in a formed tampon product. Eliminating an axial compression stage from the tampon forming process may minimize certain compression forces on the tampon pledget during the tampon forming process, and may create a relatively consistent density profile along the length of the formed or stabilized tampon product. As a result, tampons made in accordance with certain embodiments of this invention may have an improved surface appearance and/or improved re-expansion abilities.

Section A below describes terms for assisting the reader in understanding features of the invention, but not introducing limitations in the terms inconsistent with the context with which they are used in the specification. Section B is a detailed description of the drawings illustrating an apparatus in accordance with embodiments of this invention. Section C describes methods of manufacturing tampons in accordance with embodiments of this invention and Section D describes tampons made in accordance with this invention.

A. Terms

As used herein, "compression" refers to the process of pressing, squeezing, compacting or otherwise manipulating the size, shape, and/or volume of a material to obtain a tampon having a vaginally insertable shape. The term "compressed" refers to the state of a material or materials subsequent to compression. Conversely, the term "uncompressed" refers to the state of a material or materials prior to compression. The term "compressible" is the ability of a material to undergo compression.

As used herein, "mold" refers to a structure for shaping a pledget during compression and/or retaining the shape for a compressed pledget subsequent to compression during the stabilization process. Molds have an inner surface defining an inner cavity and an outer surface. The inner cavity is structured to define or mirror the shape of the compressed absorbent pledget. Thus, in some embodiments the pledget conforms to the shape of the inner cavity of the mold by a restraining force to result in a self-sustaining shape and is retained in the inner cavity during the stabilization process. In other embodiments, the mold retains the shape of the compressed pledget during the stabilization process. The inner cavity may be profiled to achieve any suitable shape including, but not limited to, cylindrical, oval, rectangular, triangular, trapezoidal, semi-circular, hourglass, serpentine or other suitable shapes. The outer surface of the mold is the surface external to the inner surface and can be profiled or shaped in any manner, such as, rectangular, cylindrical or oblong. The mold may comprise one or more members. Suitable molds used in embodiments of the invention may include, but may not be limited to unitary molds, comprising one member, and split cavity molds. Examples of split cavity molds include those disclosed in U.S. patent application Ser. No. 10/150,050 entitled "Substantially Serpentine Shaped Tampon," and U.S. patent application Ser. No. 10/150,055, entitled "Shaped Tampon," both filed on Mar. 18, 2002.

As used herein the term "pledget" refers to a construction of absorbent material prior to the compression of such construction into a tampon.

As used herein, "self-sustaining" is a measure of the degree or sufficiency to which the tampon retains its compressed form after stabilization such that in the subsequent absence of external forces, the resulting tampon will tend to retain its vaginally insertable shape and size. It will be understood by one of skill in the art that this self-sustaining form need not, and may not persist during actual use of the tampon. That is, once the tampon is inserted into the vagina or other body cavity and begins to acquire fluid, the tampon will begin to expand and may lose its self-sustaining form.

The term "shaped tampons," as used herein, refers to compressed pledgets having either a substantially serpentine shape, an "undercut" or "waist," or a non-uniform cross-section traversing from the insertion end to the withdrawal end of the tampon. The phrase "substantially serpentine" refers to a non-linear dimension between any two points spaced at least about 5 mm apart. The term "undercut" refers to tampons having a protuberance or indentation that impedes the withdrawal from a unitary mold. For example, shaped tampons may be hourglass shaped having at least one perimeter in the center of the tampon or "waist" that is less than both an insertion end perimeter and a withdrawal end perimeter.

As used herein, the term "split cavity mold" is a mold comprised of two or more members that when brought together complete the inner cavity of the mold. Each member of the split cavity mold comprises at least a portion of the inner surface that when brought together or closed completes the mold structure. The split cavity mold is designed such that at least two or more of the mold members can be at least partially separated, if not fully separated, typically after the tampon has acquired a self-sustaining shape, to expand the cavity volume circumscribed by the inner surface(s) thus permitting the easier removal of the tampon from the mold. Partial separation can occur when only a portion of two mold members are separated while other portions of the two mold members remain in contact. Where each member's inner surface portion joins the inner surface portion of another member, those points of adjacency can define a straight line, a curve, or another seam of any convoluted intersection or seam of any regular or irregular form. The elements of the split cavity in some embodiments may be held in appropriate position relative to each other by linking elements of any form including bars, rods, linked cams, chains, cables, wires, wedges, screws, etc.

The term "stabilized," as used herein, refers to a tampon in a self-sustaining state wherein it has overcome the natural tendency to re-expand to the original size, shape and volume of the absorbent material and overwrap, which comprise the pledget. Likewise the term "stabilization," as used herein, refers to a process to stabilize or otherwise facilitate stabilizing a tampon in a self-sustaining state.

As used herein the term "tampon," refers to any type of absorbent structure that is inserted into the vaginal canal or other body cavity for the absorption of fluid therefrom, to aid in wound healing, or for the delivery of active materials, such as medicaments, or moisture. The tampon may be compressed into a generally cylindrical configuration in the radial direction, axially along the longitudinal axis or in both the radial and axial directions. While the tampon may be compressed into a substantially cylindrical configuration, other shapes are possible. These may include shapes having a cross section that may be described as oval, rectangular, triangular, trapezoidal, semi-circular, hourglass, serpentine, or other suitable shapes. Tampons have an insertion end, withdrawal end, a length, a width, a longitudinal axis and a radial axis. The tampon's length can be measured from the insertion end to the withdrawal end along the longitudinal axis. A typical compressed tampon for human use is within a range from about 30 mm to about 60 mm in length. A tampon may be straight or non-linear in shape, such as curved along the longitudinal axis. A typical compressed tampon is within a range from about 8 mm to about 20 mm wide. The width of a tampon, unless otherwise stated in the specification, corresponds to the distance across the largest cross-section, along the length of the tampon and perpendicular to the longitudinal axis of the tampon.

The term "vaginal cavity," "within the vagina," and "vaginal interior," as used herein, are intended to be synonymous and refer to the internal genitalia of the mammalian female in the pudendal region of the body. The term "vaginal cavity" as used herein is intended to refer to the space located between the introitus of the vagina (sometimes referred to as the sphincter of the vagina or hymeneal ring,) and the cervix. The terms "vaginal cavity," "within the vagina" and "vaginal interior," do not include the interlabial space, the floor of vestibule or the externally visible genitalia.

As used herein, "cm" is centimeter, "g" is grams, "g/cc" is grams per cubic centimeter, "g/m$^2$" is grams per meter squared, "L" is liters, "L/s" is liters per second, "mL" is milliliters", "mm" is millimeters, "min" is minutes, "psi" is pounds per square inch, "rpm" is rate per minute, and "s" is seconds.

The term "crease" as used herein, is the configuration of the compressed pledget that may be incidental or deliberate to compaction of the pledget. The creased configuration may be characterized by at least one bend at least in a portion of the pledget such that portion of the pledget may be positioned with a different plane than before with the observation that the surface regions near the bend may be in a different distal and angular relationship to each other after the folding has taken place. The term "crease" encompasses folds and wrinkles. In the case of the lateral compaction of a generally flat pledget, there may exist one or more creases in the form of bends or folds of generally 180 degrees such that the surface regions on either side of the bend may be juxtaposed or even in co-facial contact with each other.

As used herein, the "tampon compression crossdie" is a machine assembly that includes parts that may compress a pledget. Typically a pledget compressed in the tampon compression crossdie is then transferred to a mold for final shaping into a self-sustaining form of a vaginally insertable shape where, the mold may further compress parts of the pledget beyond that which the tampon compression crossdie accomplished prior.

As used herein, the "compression member" or "force application member" is any member that can be used to compress a pledget. It can also function to transfer a compressed pledget which has been stabilized into a formed tampon.

As used herein, "actuating" is any force delivered by an electric motor, mechanical transmission, pneumatically, linear drive, manual, and/or hydraulic.

As used herein, a "high aspect ratio shape" is any shape in which the length is greater than the diameter or width of the shape. The shape may not necessarily contain any defined circles, arcs, or cross-sectional portions.

As used herein, "relatively smooth" is defined as a surface relatively free from irregularities, roughness, or projections greater than about 1 mm in height or depth as measured from the surface.

As used herein, a "density profile" is defined as the density of a material in a lateral cross-section of a tampon. The phrase "substantially consistent density profile" is defined as a comparison between at least two lateral cross-sections of a tampon, wherein the densities between the cross-sections are substantially similar.

B. Tampon Manufacturing Apparatus

Turning to FIG. 1, an uncompressed pledget 10 of absorbent material 12 is illustrated. The uncompressed pledget 10 may be compressed to form a tampon in accordance with an embodiment of this invention. The uncompressed pledget 10 extends from an insertion end 14 to a withdrawal end 16 with opposing sides 18 and 20 extending from the insertion end 14 to the withdrawal end 16. A withdrawal cord or drawstring 22 may be connected to and extend from a portion of the uncompressed pledget, such as the insertion end 14 or the withdrawal end 16 of the uncompressed pledget 10.

Although the uncompressed pledget 10 is illustrated as having a generally square or rectangular shape, the uncompressed pledget 10 can have a variety of shapes including, but not limited to, oval, round, chevron, square, rectangular, and the like. The uncompressed pledget 10 may have a length L1 extending from the insertion end 14 to the withdrawal end 16 of the uncompressed pledget 10, a width W1 extending from the one side 18 of the uncompressed pledget 10 to the other side 20 and perpendicularly to the length L1, and a thickness T1 extending perpendicularly to both the length L1 and width W1 of the uncompressed pledget 10.

The absorbent material 12 of the uncompressed pledget 10 may be constructed from a wide variety of liquid absorbing materials commonly used in absorbent articles. Such materials include but are not limited to rayon (such as GALAXY rayon, SARILLE L rayon both available from Accordis Kelheim GmbH of Kelheim, Germany), cotton, folded tissues, woven materials, nonwoven webs, synthetic and/or natural fibers or sheathing, comminuted wood pulp which is generally referred to as airfelt, or combinations of these materials. Other materials that may be incorporated into the pledget 10 include peat moss, absorbent foams (such as those disclosed in U.S. Pat. No. 3,994,298 issued to Desmarais on Nov. 30, 1976 and U.S. Pat. No. 5,795,921 issued to Dyer, et al.), capillary channel fibers (such as those disclosed in U.S. Pat. No. 5,356,405 issued to Thompson, et al. issued on Oct. 18, 1994), high capacity fibers (such as those disclosed U.S. Pat. No. 4,044,766 issued to Kaczmarck, et al. on Aug. 30, 1994), and super absorbent polymers or absorbent gelling materials (such as those disclosed in U.S. Pat. No. 5,830,543 issued to Miyake, et al. on Nov. 3, 1998). A more detailed description of liquid absorbing materials can be found in U.S. Pat. No. 6,740,070 to Raymond Agyapong.

The uncompressed pledget 10 may optionally include an overwrap comprising materials such as rayon, cotton, bicomponent fibers, polyethylene, polypropylene, other suitable natural or synthetic fibers known in the art, and mixtures thereof In some embodiments, the uncompressed pledget 10 has a nonwoven overwrap comprised of bicomponent fibers that have a polypropylene core surrounded by polyethylene manufactured by Vliesstoffwerke Christian Heinrich Sandler GmbH and Company KG (Schwarzenbach/Salle Germany) under the trade name SAS B31812000. In other embodiments, the tampon may comprise a nonwoven overwrap of a hydro entangled blend of 50% rayon, 50% polyester available as BBA 140027 produced by BBA Corporation of South Carolina, US. In certain embodiments, the overwrap may be treated to hydrophilic, hydrophobic, wicking or nonwicking.

The uncompressed pledget 10 may optionally include a secondary absorbent member, an additional overwrap, a skirt portion and/or an applicator. The withdrawal cord 22 attached to the uncompressed pledget 10 may be made of any suitable material in the prior art such as cotton and rayon. U.S. Pat. No. 6,258,075 issued to Taylor et al. describes a variety of secondary absorbent members for use in pledgets. An example of a skirt portion is disclosed in U.S. Pat. No. 6,840,927 to Margaret Hasse.

Figure 20:
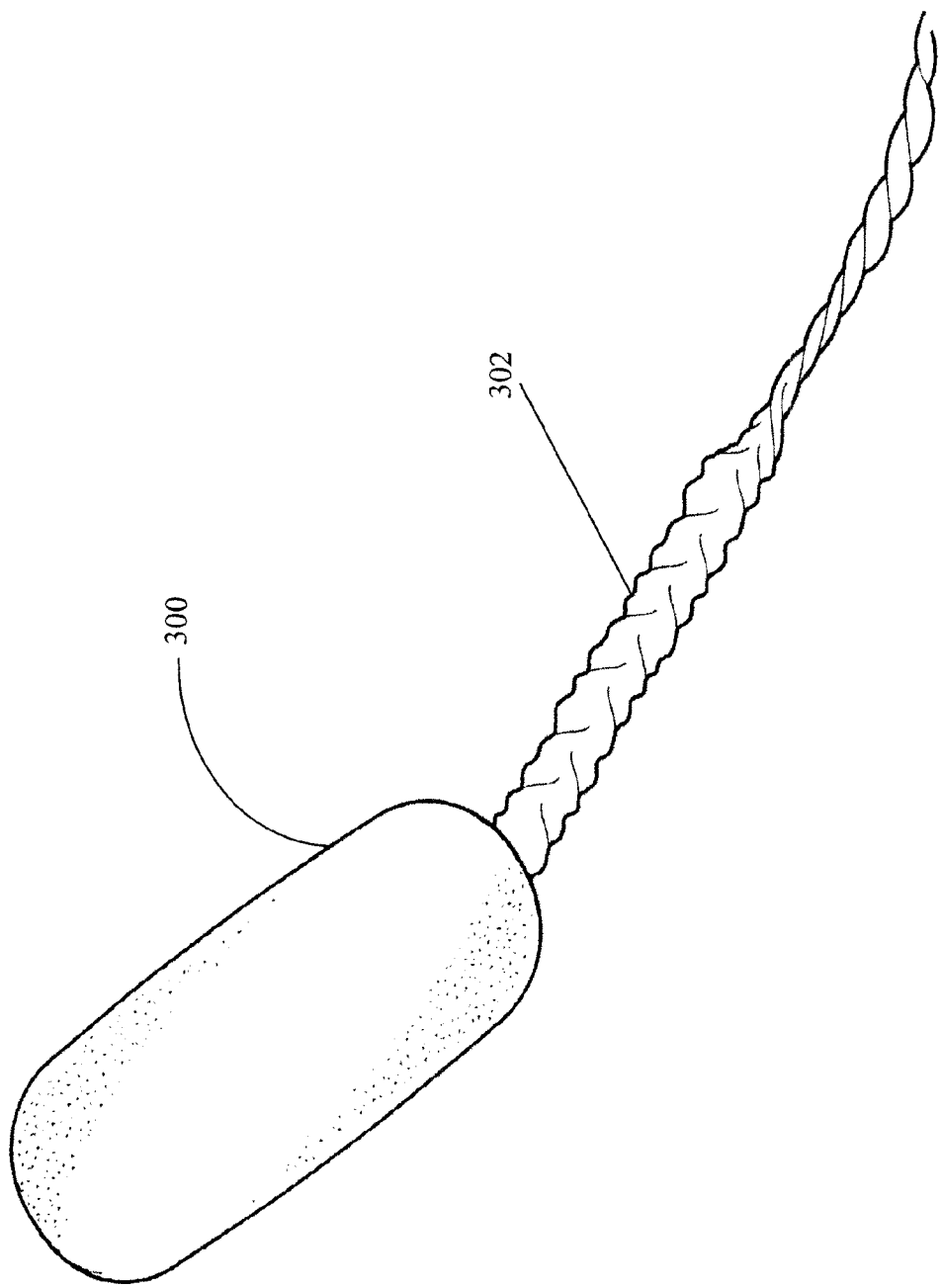
FIG. 20 is a perspective view a tampon made in accordance with an embodiment of this invention.

A tampon forming apparatus 100 for making tampons in accordance with an embodiment of this invention is illustrated in FIGS. 2-8. One example of a suitable tampon that can be manufactured with the tampon forming apparatus 100 is illustrated in FIG. 20. The tampon forming apparatus 100 may generally comprise a tampon compression crossdie 102 for initially compressing the uncompressed pledget 10 of absorbent material to form a compressed pledget 104, a split cavity mold 106 for receiving an uncompressed pledget 10 and setting the uncompressed pledget 10 in a self-sustaining shape, such as a formed tampon, and a transfer member 108 for pushing the uncompressed pledget 10 into the split cavity mold 106 and ejecting the compressed pledget 104, which has been set into a self-sustaining shape, such as a formed tampon, from the split cavity mold 106. In certain embodiments, a split cavity mold such as 106 can be referred to as a "compression/stabilization mold."

Figure 3:
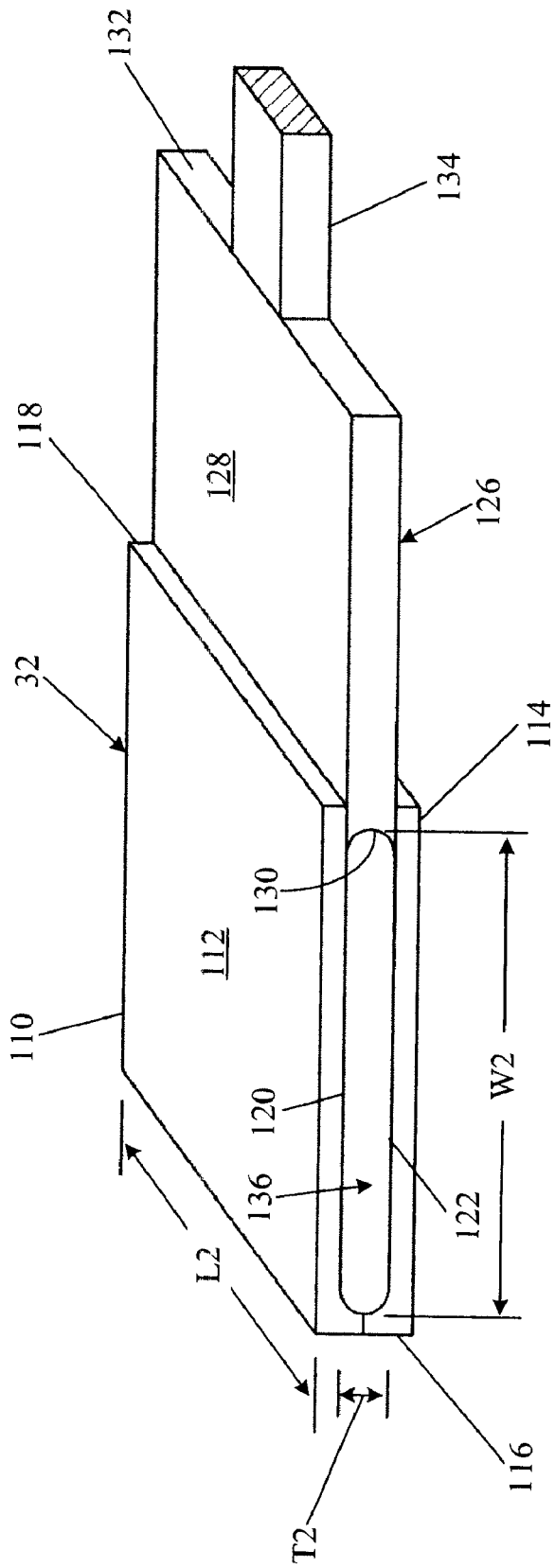
FIG. 3 is a perspective view of the tampon compression crossdie of FIG. 2 in an open position.
Figure 4:
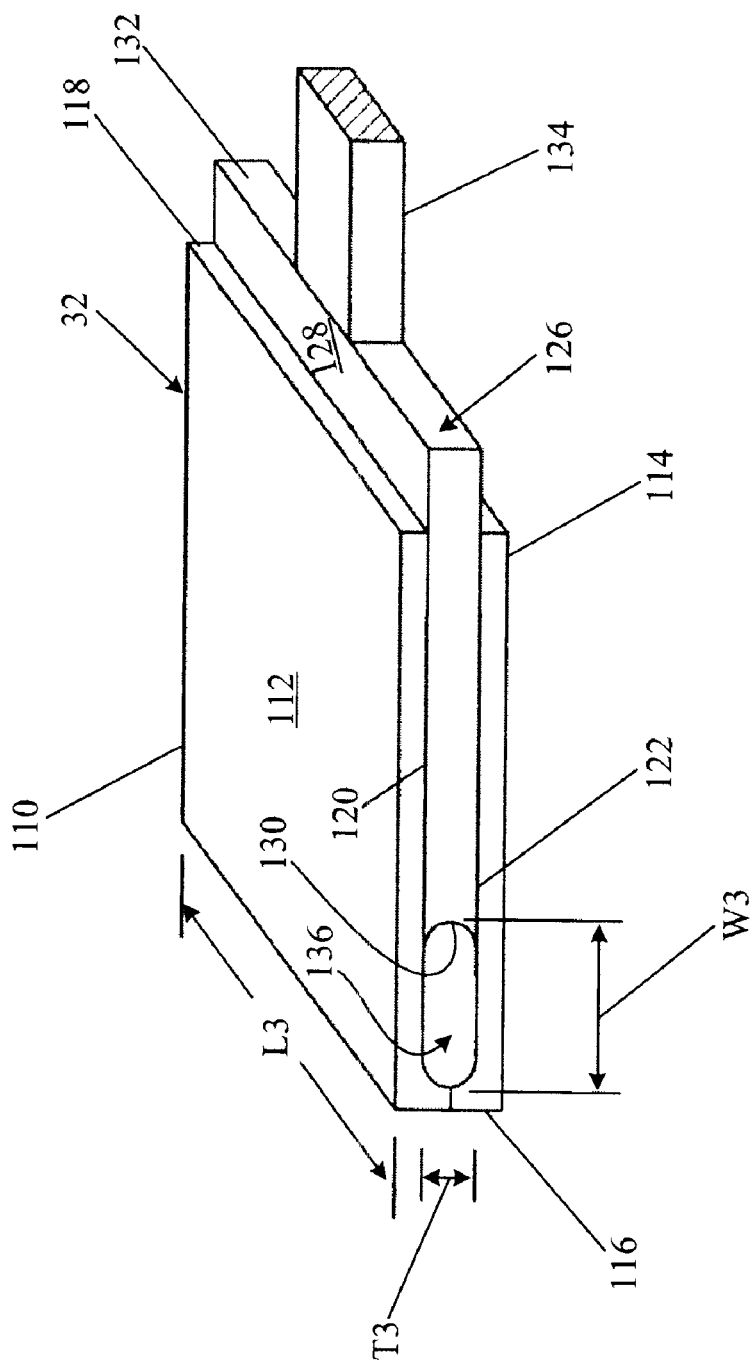
FIG. 4 is a perspective view of the tampon compression crossdie of FIG. 2 in a compression position.

The tampon compression crossdie 102 may comprise a u-shaped anvil 110, as shown in FIGS. 3 and 4. The tampon compression crossdie 102 may comprise a top plate 112 and a juxtaposed bottom plate 114 extending from an end wall 116 connecting the top and bottom plates 112 and 114 to an open end 118 thereby forming a channel 120 between the top and bottom plates 112 and 114. The channel 120 may extend from an inlet end 122 to a discharge end 124 of the anvil 110. The tampon compression crossdie 102 may also comprise a die or force application member 126 comprising a solid plate 128 extending from a leading end 130 to a trailing end 132 and an actuating rod 134 connected to the trailing end 132 for reciprocating the die or force application member 126 within the channel 120 of the anvil 110. The leading end 130 of the die or force application member 126 and the top and bottom plates 112 and 114 and end wall 116 of the anvil 110 may form a compression machine cavity 136 within the channel 120 of the anvil 110 for receiving the uncompressed pledget 10. The die or force application member 126 may compress the uncompressed pledget 10 in the compression machine cavity to form the compressed pledget 104.

In certain embodiments, opposing plates, such as 112 and 114, with end walls on opposing ends may move relative to each other and thereby compress the uncompressed pledget 10. For example, respective drive mechanisms can be mounted to each opposing plate to manipulate each plate separately and independently from each other. In other embodiments, opposing plates, such as 112 and 114, may have other shapes and may move relative to each other and thereby compress the uncompressed pledget 10. Other configurations for the tampon compression crossdie 102 for carrying out the functions described herein will be apparent to those skilled in the art from reading the details of this specification.

The compression machine cavity 136 of the tampon compression crossdie 102 may have an oval cross sectional shape as illustrated in FIGS. 3 and 4, but it should be understood that the compression machine cavity 136 may have other shapes as well including, but not limited to, round, square, polygonal, and rectangular cross-sectional shapes depending on the desired shape or cross-section for a stabilized pledget or formed tampon. It should also be understood that the compression machine cavity 136 may have a cross-sectional shape of varying or otherwise irregular width depending on the desired shape or cross-section for a compressed pledget, such as 104.

Furthermore, the top and bottom plates 112 and 114, the end wall 116 of the anvil 110, and the leading end 130 of the die or force application member 126 may be relatively smooth. Some or all of these elements may include one or more patterns, pattern structures, or contoured shapes for impressing a corresponding patterned or contoured impression in a portion of the compressed pledget, such as 104. Patterns, pattern structures, or contoured shapes can include, but are not limited to, a convex-shaped element, a concave-shaped element, a combination of both a convex-shaped element and a concave-shaped element, an axially-oriented element, a laterally-oriented element, or a pattern with both axially-oriented and laterally-oriented elements.

Figure 4A:
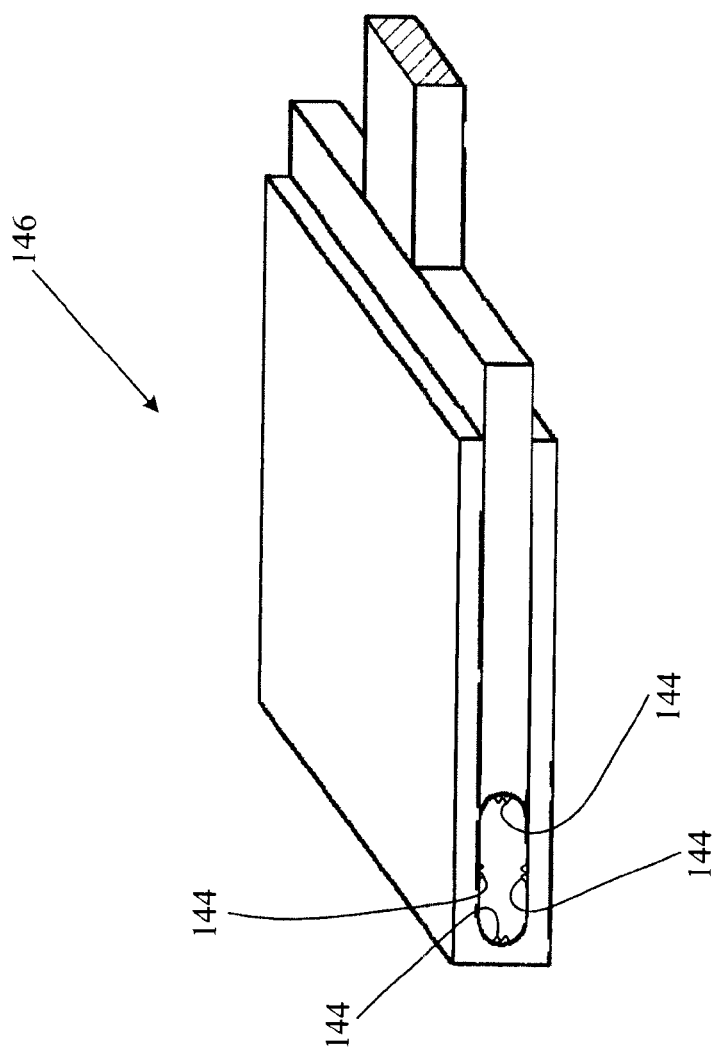
FIG. 4A is a perspective view of one embodiment of a tampon compression crossdie with a pattern structure in accordance with an embodiment of the invention.

An example of a pattern structure associated with a tampon compression crossdie is shown in FIG. 4A. In this example, a pattern structure 144 can be machined or otherwise mounted to a portion of the crossdie 146. The pattern structure 144 shown can impress a corresponding patterned or contoured impression in a portion of a compressed pledget, such as 104.

In certain embodiments, at least one header for forming a patterned impression in at least one end of the compressed pledget, such as 104, can be used. In these embodiments, for example, the die or force application member 126 may be used to impart a force on one end of the compressed pledget 104 such that the opposing end may contact the at least one header to form a patterned impression in an end of the compressed pledget 104. In another example, at least one header may be moved to contact at least one end of the compressed pledget 104 to form a patterned impression in an end of the compressed pledget 104. Examples of headers and suitable equipment for forming patterned impressions in at least one end of a compressed pledget are disclosed in U.S. patent application Ser. No. 11/799,914, filed May 3, 2007, entitled "Tampon with Patterned End and Method and Apparatus for Making the Same."

When in an open configuration as illustrated in FIG. 3, the compression machine cavity 136 may have a length L2 extending from the inlet end 122 of the anvil 110 of the discharge end 124, a width W2 extending from the interior of the anvil end wall 116 to the leading end 130 of the die or force application member 126 and perpendicular to the length L2, and a thickness T2 extending from the interior of the top plate 112 of the anvil 110 to the bottom plate 114 perpendicular both to the length L2 and width W2 of the compression machine cavity 136. In some embodiments, the width W2 of the compression machine cavity 136 when the compression machine cavity 136 is in an open configuration may be close to or greater than the width W2 of the uncompressed pledget 10. In certain embodiments, the length L2 of the compression machine cavity 136 may also be close to or relatively greater than the length L1 of the uncompressed pledget 10 and the thickness T2 of the compression machine cavity 136 may be close to or relatively smaller than the uncompressed pledget thickness T1. For example, respective drive mechanisms can be mounted to opposing plates, such as 112 and 114, or other components to manipulate each plate and/or component separately and independently from each other.

When in a compression configuration as illustrated in FIG. 4, the compression machine cavity 136 may have a length L3 which is the same as or relatively smaller than the length L2 in the open configuration and a thickness T3 which is same as or relatively smaller thickness as T2 in the open configuration, but may have a width W3 which may be substantially less than the width W2 of the compression machine cavity 136 in the open configuration and may be substantially less than the width W1 of the uncompressed pledget 10. In certain embodiments when the uncompressed pledget 10 is compressed in the tampon compression crossdie 102, the compressed pledget may adopt the cross-sectional shape and width and thickness of the compression machine cavity 136 in the compressed configuration. Thus, the compressed pledget may have an approximate width of W3 and an approximate thickness of T3. The manner of actuation of the die or force application member 126 within the anvil channel 120 to compress the pledget 10 may be by any suitable means to drive the actuating rod 134.

The degree of compression of the uncompressed pledget 10 in the compression machine cavity 136 in the widthwise direction may be a major component of the compression. In accordance with certain embodiments of this invention, the major compression of the uncompressed pledget in the compression machine cavity 136 in the widthwise direction is within a range from about 65% to about 90% of the original width of the uncompressed pledget 10. The degree of compression of the uncompressed pledget 10 in the thickness and lengthwise directions may be a minor component of the compression and, in accordance with certain embodiments of this invention, the minor compression of the uncompressed pledget 10 in the compression machine cavity 136 in the thickness and lengthwise directions may be no more than about 40% of the original width of the uncompressed pledget 10. It should be understood that it is contemplated in certain embodiments of the invention that there may be no compression of the uncompressed pledget 10 in the lengthwise and/or thickness directions.

According to certain embodiments, the compressed pledget 104 may be heated in the compression machine cavity 136 to impart a self-sustaining shape to the compressed pledget 104 and resulting tampon. Methods of setting or stabilizing the tampon shape include heating the compressed pledget 104 with steam as disclosed in U.S. patent application Ser. No. 10/887,645 or thermal temperature gradient conduction or microwaving, as disclosed in U.S. Pat. No. 7,047,608. Various methods involving heat conduction, radiant heat, and microwaves can be used in accordance with various embodiments of the invention. In certain embodiments, a heated gas or other medium can be applied to the compressed pledget 104 via at least one pore or fluid communication passage while the compressed pledget 104 is within the closed compression machine cavity 136. Methods of setting or stabilizing the tampon shape in this manner are disclosed in U.S. patent application Ser. No. 10/887,645, filed Jul. 9, 2004, entitled "Compressed, Gas-Stabilized Tampon Having Multiple Folds;" U.S. patent application Ser. No. 11/595,322, filed Nov. 10, 2006, entitled "System and Method for an Expandable Pushrod Mold Seal;" and U.S. patent application Ser. No. 11/601,946, filed Nov. 20, 2006, entitled "Method and Apparatus for Producing Stabilized Absorbent Article."

A variety of materials may be used to make the components of the tampon forming apparatus 100. Suitable materials may be relatively rigid and include, but are not limited to stainless steel, and in the case of microwave heat stabilization, microwave safe materials.

Figure 5:
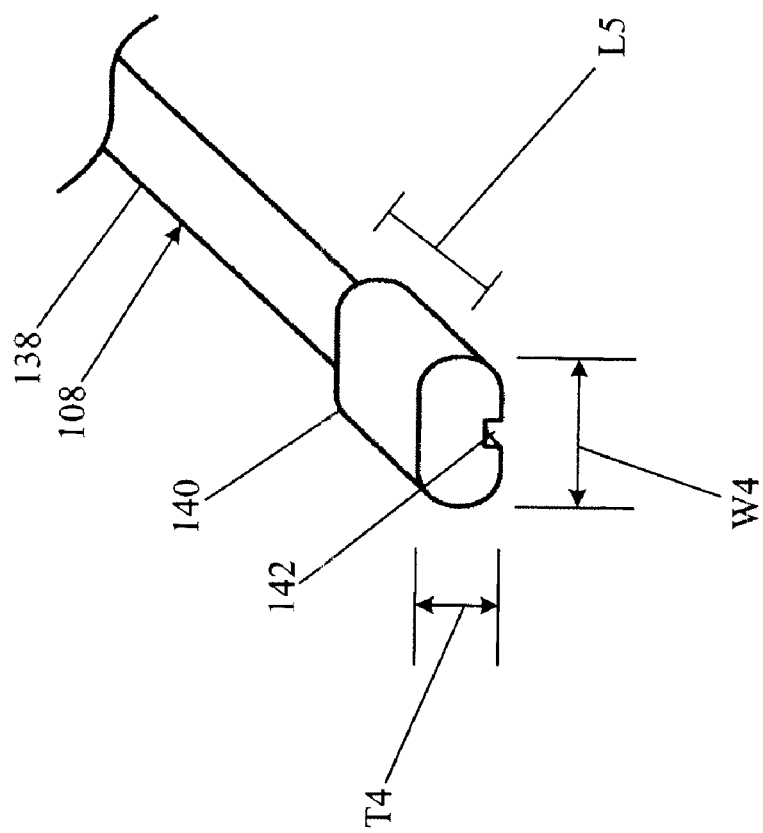
FIG. 5 is a partial perspective view of the compression member which forms part of the tampon forming apparatus in FIG. 2.

As shown in FIG. 5, the transfer member 108 may comprise an actuating rod 138 and a head 140 connected to the actuating rod 138 for contacting the formed tampon 104 to push the formed tampon 104 from the compression machine cavity 136. The cross-sectional shape of the compression member head 140 may be similar to and, in certain embodiments, substantially identical to the cross-sectional shape of the compression machine cavity 136 in the compressed configuration. In certain embodiments, the compression member head 140 may have a width W4 and a thickness T4 extending perpendicularly to the head width. In certain embodiments, the compression member head 140 may have another geometry, configuration, or shape. For example, a compression member head, such as 140, may have a contoured shape with a pattern or pattern structure for impressing a corresponding contoured shape and patterned impression in a portion of the compressed pledget, such as 104.

Figure 5A:
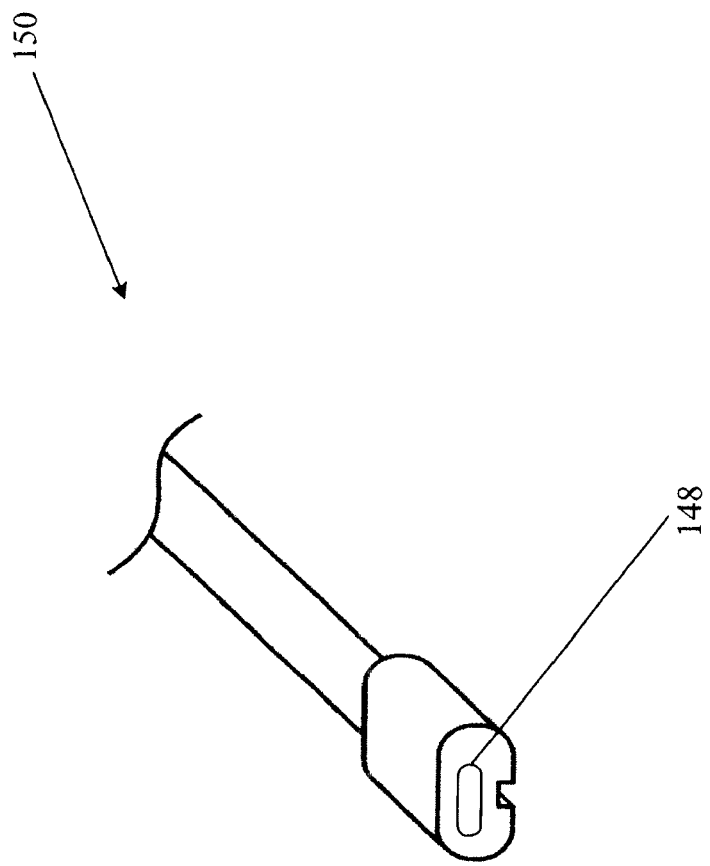
FIG. 5A is a partial perspective view of one embodiment of a compression member with a pattern structure in accordance with an embodiment of the invention.

An example of a pattern structure associated with a compression member head is shown in FIG. 5A. In this example, a pattern structure 148 can be machined or otherwise mounted to a portion of a contoured compression member head 150. The pattern structure 148 shown can impress a corresponding patterned or contoured impression in a portion of a compressed pledget, such as 104.

The compression member head 140 may have a slot 142 therein for receiving the withdrawal cord 22 of the formed tampon 104 so that the withdrawal cord 22 is not cut by the compression member head 140 when the compression member head 140 transfers or discharges the formed tampon 104 from the compression machine cavity 136.

In certain embodiments, the formed tampon 104, the compression machine cavity 136 in the compressed configuration, and the compression member head 140, each may have cross-sectional shapes and dimensions which are very similar and, in certain embodiments, even substantially identical. These close tolerances may help avoid trapping of fibers from the formed tampon 104 as the compression member head 140 transfers or discharges the formed tampon 104 from the compression machine cavity 136. Trapped fibers may create binding and shearing forces that may damage the tampon forming apparatus 102 or the formed tampon 104, or both.

In other embodiments, the formed tampon 104, the compression machine cavity 136 in the compressed configuration, and the compression member head 140, each may have cross-sectional shapes and dimensions which are very dissimilar and, in certain embodiments, even substantially non-identical. In these instances, coordination between the compression member head 140 and the compression machine cavity 136 should be controlled to minimize damage to the tampon forming apparatus 102 or the formed tampon 104, or both, when the formed tampon 104 is removed from the compression machine cavity 136.

Figure 9:
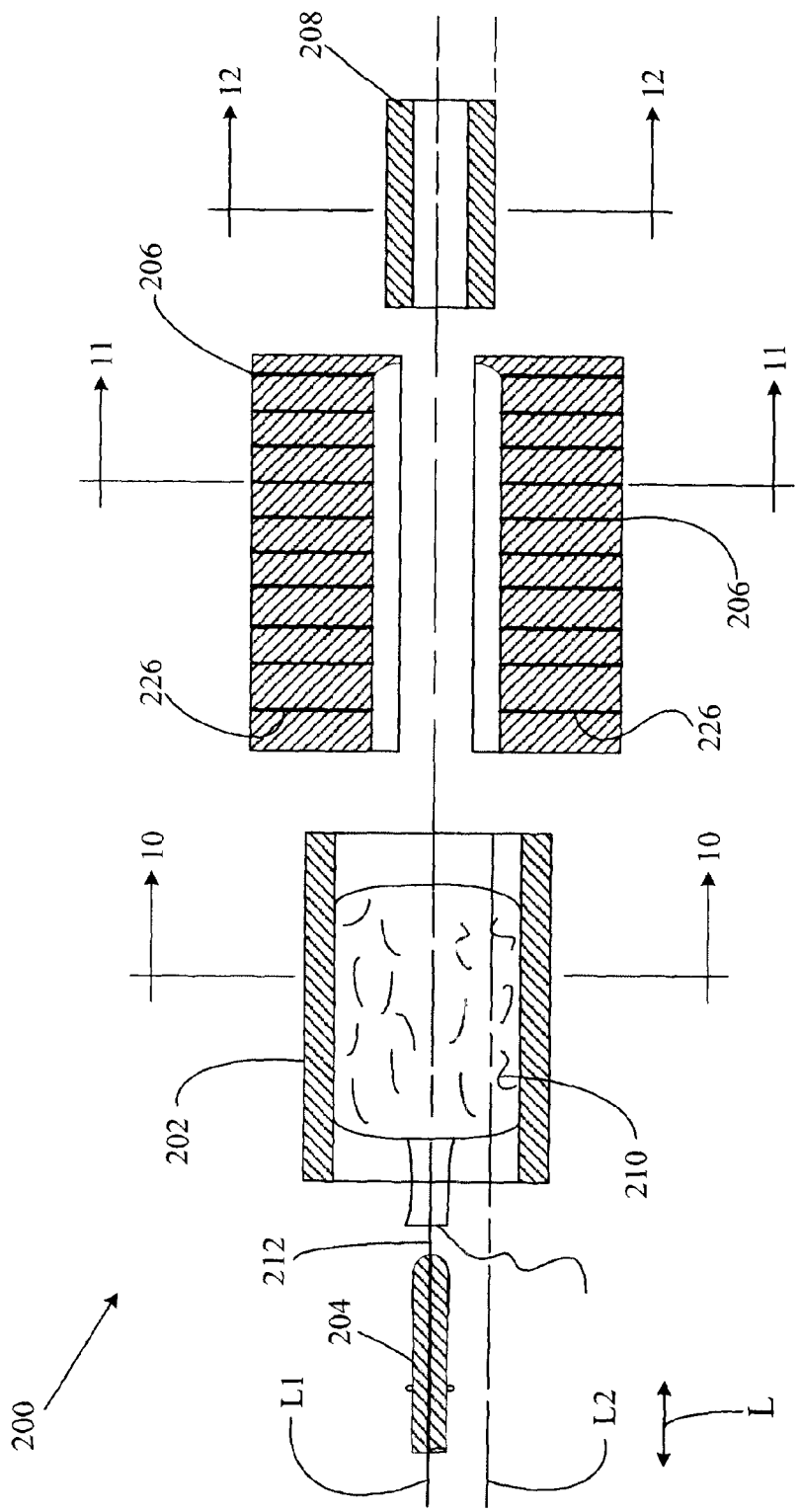
FIG. 9 is a cross-sectional view of one system embodiment of the invention.

Another tampon forming apparatus 200 for making tampons in accordance with an embodiment of this invention is illustrated in FIGS. 9-19. FIG. 9 is a cross-sectional view of an embodiment of the tampon forming apparatus 200 which may include a pledget infeed carrier 202, a transfer member 204, a split cavity mold or compression/stabilization mold 206, and a product discharge carrier 208. In certain embodiments, the steps of compressing and stabilizing of a tampon pledget may be implemented while the tampon pledget is within a single split cavity mold or compression/stabilization mold, such as 202, in order to reduce or eliminate the step of transferring a compressed pledget from a compression mold to a separate stabilization mold.

In FIG. 9, the compression/stabilization mold 206 is shown in an open position and aligned with the pledget infeed carrier 202 and a product discharge carrier 208. This embodiment shows a transfer member 204, or "pushrod," and a pledget 210 disposed in the pledget infeed carrier 202. The transfer member 204 can serve one or more functions, such as, for example: (a) transferring the pledget 210 through the sequence of process steps taking place during traveling of the pledget 210 from the pledget infeed carrier 202 to the compression/stabilization mold 206, and to the product discharge carrier 208; and (b) optionally compressing the pledget 210 longitudinally (in addition to the compression in the radial direction provided by the compression/stabilization mold 206, as described below); (c) optionally forming a desired shape cavity at the base region of the product, suitable for the user's finger to facilitate digital insertion of the product into the vaginal (or other) cavity; and/or (d) providing a suitable seal for containing a gas inside the compression/stabilizing mold 206 during the stabilization treatment of the tampon.

The transfer member 204 may include at least one needle 212 extending from the transfer member 204 longitudinally for discharging a stabilized product from the compression/stabilization mold 206. The transfer member 204 may be aligned with the pledget infeed carrier 202, the compression/stabilization mold 206, and the tampon discharge carrier 208 along a first longitudinal centerline L1.

It should be noted that a pledget having a secondary absorbent member extending from the base region of the pledget may be loaded into the pledget infeed carrier 202 with the secondary absorbent member being diverted radially in relation to the pledget to ensure that the secondary absorbent member does not interfere with the movement of the transfer member 204. This may reduce or prevent pushing the secondary absorbent member into the base region of the pledget. The radial diversion of the secondary absorbent member (including with at least one cord extending also from the base region of the tampon) can be provided during loading of the pledget by any suitable means, for example, a plate disposed in the direction of loading of the pledget into the cavity of the pledget infeed carrier 202. Alternatively, a vacuum tube could be used.

Figures 10, 11:
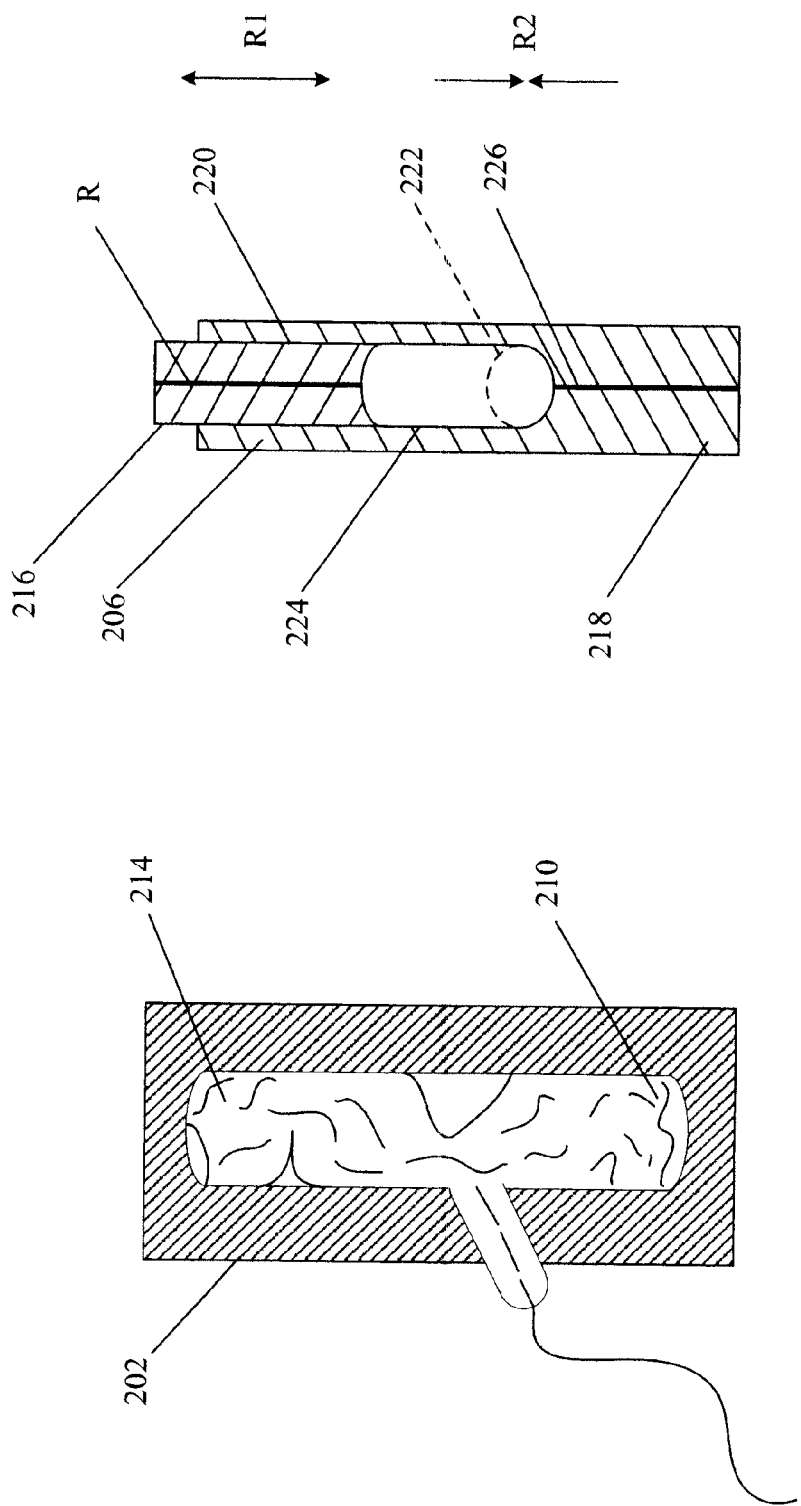
FIG. 10 is a cross-sectional view of the split compression mold of FIG. 9, taken along line 10-10.
FIG. 11 is a cross-sectional view of the split stabilization mold of FIG. 9, taken along line 11-11.

FIG. 10 is a cross-sectional view of the pledget infeed carrier 202 of FIG. 9, taken along line 10-10. The pledget infeed carrier 202 includes a cavity 214 that can be suitably shaped to accept the pledget 210, which is shown as being folded to form an M-shape configuration. However, alternatively, the pledget 210 can be unfolded or folded into any suitable configuration. In addition, the orientation of the pledget 210 within the cavity 214 can vary, and may be unfolded or folded into any suitable configuration within the cavity 214. The pledget infeed carrier 202 can be made from any material suitable for producing products according to embodiments of the invention.

FIG. 11 is a cross-sectional view of the compression/stabilization mold 206 of FIG. 9, taken along line 11-11. The compression/stabilization mold 206 shown in this example includes a first member 216 and a second member 218. At least one of the members 216 and 218 is capable of moving in a direction R1 to effect an open position 220 or direction R2 to effect a closed position 222 (shown as an interrupted line) of the compression/stabilization mold 206. In the closed position 222, the inner surface 224 of the compression/stabilization mold 206 forms a cross-section of any desired shape, such as a generally circular cross-section of a desired diameter, for example, a diameter D of about 12.5 mm. The inner surface 224 can be of any suitable shape and of any desired dimension, and may have any suitable pattern for forming a corresponding pattern impression on the exterior surface of a compressed pledget. The compression/stabilization mold 206 can be made from any material capable of providing desired compression forces and suitable for producing products according to embodiments of the invention.

The inner surface of the compression/stabilization mold 206 may include one or more patterns, pattern structures, or contoured shapes for impressing a corresponding patterned or contoured impression in a portion of the compressed pledget, such as 230. Patterns, pattern structures, or contoured shapes can include, but are not limited to, a convex-shaped element, a concave-shaped element, a combination of both a convex-shaped element and a concave-shaped element, an axially-oriented element, a laterally-oriented element, or a pattern with both axially-oriented and laterally-oriented elements.

In certain embodiments, the compression/stabilization mold 206 may include at least one pore 226 or other fluid communication passage suitable for providing a gas or medium flow inside the inner surface of the compression/stabilization mold 206. Such pores or other fluid communication passages can be utilized to create pre-folding, folding, or other manipulation of a pledget within a compression/stabilization mold 206. Examples of systems and processes to create folding and other manipulation of a pledget within a compression/stabilization mold are described in U.S. patent application Ser. No. 11/504,983, filed Aug. 16, 2006, entitled "A Process for Producing Folded and Compressed Tampons."

In certain embodiments, once a pledget is within a compression/stabilization mold, such as 206, pre-folding, folding, or other manipulation can occur at the point of one or more pores or fluid communication passages, such as 226, thereby facilitating greater control of folding for better uniformity of fold configuration upon compression. Pores, such as 226, can comprise fluid communication passages and force delivery means for delivering pressure to predetermined portions of a tampon pledget. Pores or fluid communication passages can comprise holes or slots, and force delivery means can comprise mechanical folding pins, fins, or pneumatic or other fluid impingement folding means, and in either embodiment the force delivery means can serve the function of accurately, consistently, and predictably pre-folding the tampon pledget into a generally zigzag or fan-folded shape such that upon compression the folds are of uniform and repeatable dimensions and the pledget can compress uniformly. This is because folding can be accomplished at the same place as compression.

Figure 12:
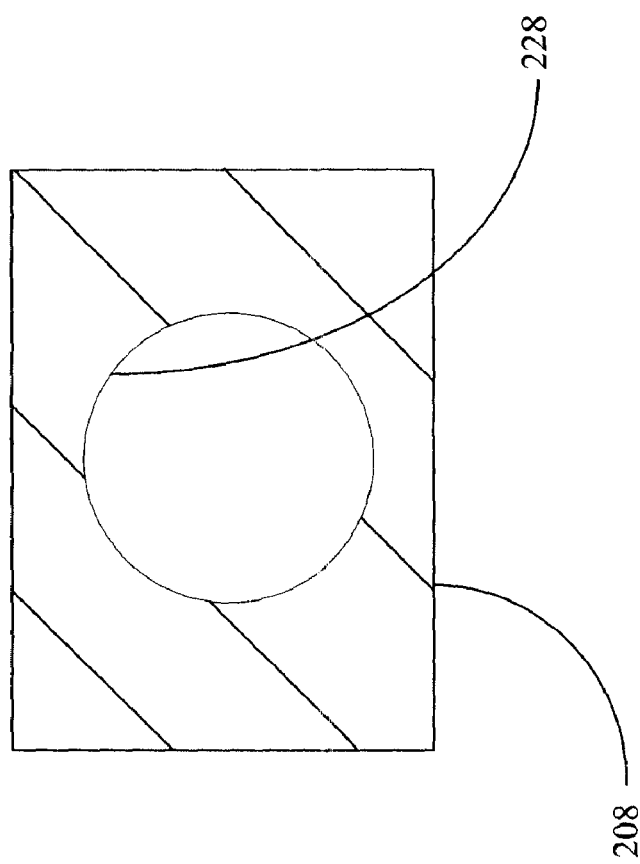
FIG. 12 is a cross-sectional view of a tampon discharge carrier of FIG. 9, taken along line 12-12.

FIG. 12 is a cross-sectional view of the product discharge carrier 208 of FIG. 9, taken along line 12-12. The product discharge carrier 208 can be slightly larger in the dimensions and makeup, in all or any aspects, to the compression/stabilization mold 206 shown in FIG. 9 and described in more detail above. The product discharge carrier 208 includes a cavity 228 that can be suitably dimensioned and shaped to accept a stabilized tampon. The product discharge carrier 208 can be made from any material suitable for facilitating the movement of stabilized products in accordance with embodiments of the invention.

Figure 13:
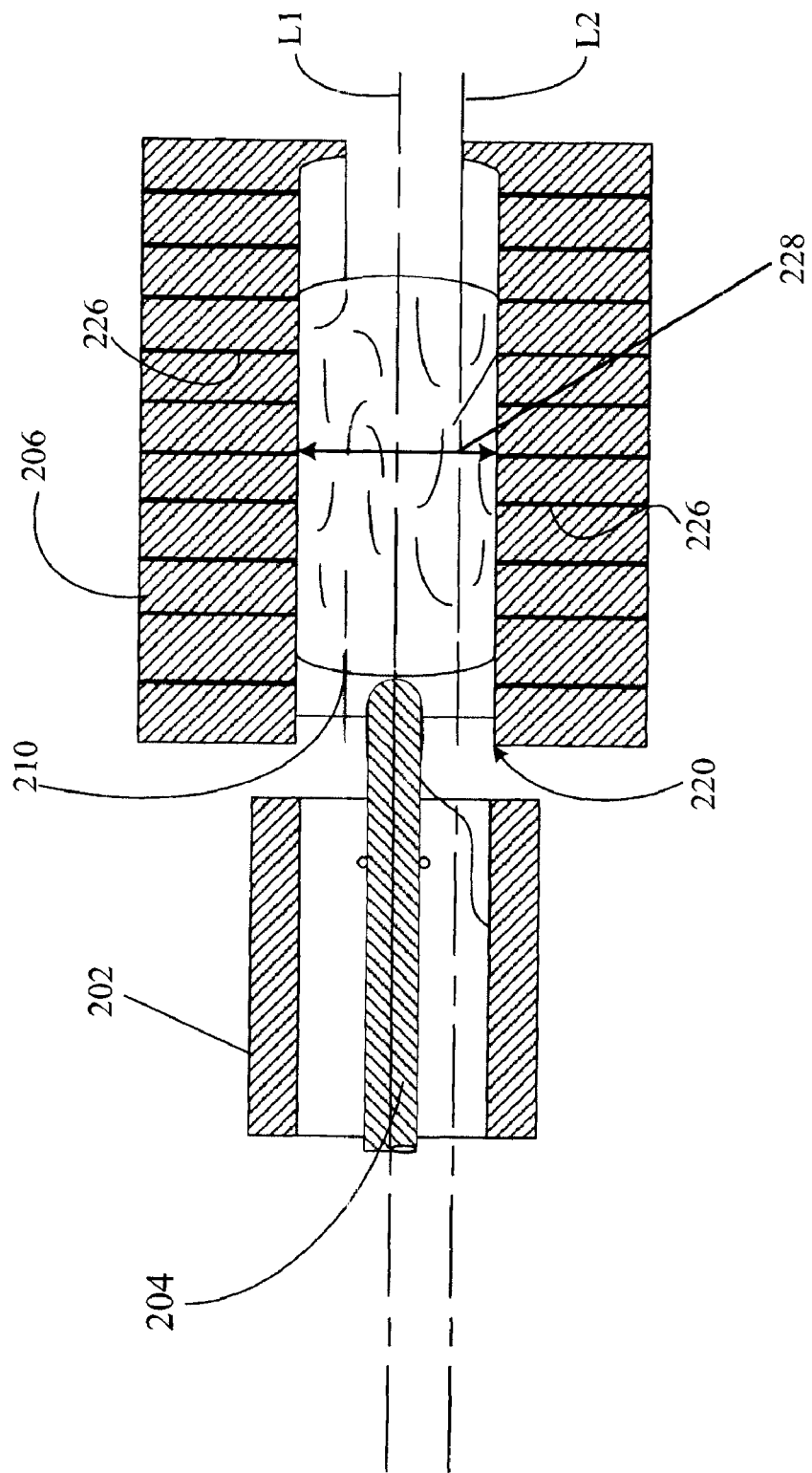
FIG. 13 is a cross-sectional view of an embodiment of the invention showing a pledget being loaded into the split compression mold by a transfer member, the split compression mold being in an open position.

FIG. 13 is a cross-sectional view of an embodiment of the invention showing a pledget 210 being loaded into the compression/stabilization mold 206 by the transfer member 204 when the compression/stabilization mold 206 is in the open position 220 and the transfer member 204 is aligned with the first longitudinal centerline L1. In the open position 220, the compression/stabilization mold 206 has an inside dimension 228 that can be any dimension suitable for accepting the pledget 210. For example, in one embodiment of the invention, the inside dimension 228 may be from about 25 mm to about 80 mm, or any number in this range. In certain embodiments, the inside dimension 228 is about 40.5 mm.

Figure 14:
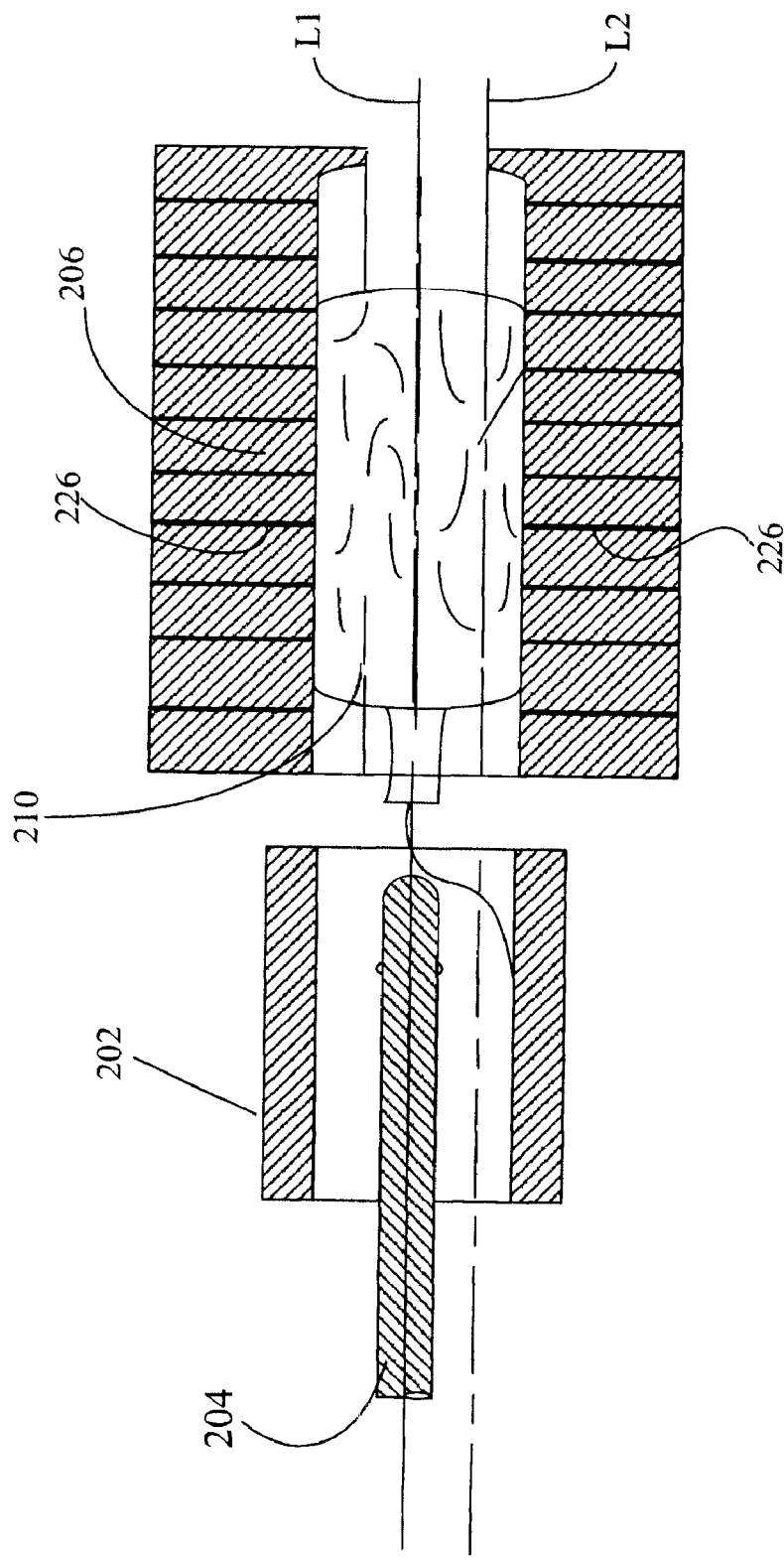
FIG. 14 is a cross-sectional view of an embodiment of the invention showing a transfer member being detracted from the pledget.

FIG. 14 is a cross-sectional view of an embodiment of the invention showing a transfer member 204 being retracted from the pledget 210 with the pledget 210 loaded in the compression/stabilization mold 206. It should be noted that the transfer member 204 may be detracted from the pledget 210 to detract the needle(s) 212 from the pledget 210 prior to the compression of the pledget 210. However, other contemplated embodiments of the transfer member 204 may allow the needle(s) 212 to move inside the transfer member 204 to protrude from or hide inside the transfer member 204, thus eliminating the need for the retraction of the transfer member 204.

It should be also noted that other contemplated embodiments of the compression/stabilization mold 206 may include moving multiple mold members, in contrast to embodiments including a moving mold member and a fixed mold member. When both moving mold members are employed, the transfer member 204 may not need to move in the direction R for closing and opening of the combined mold.

Figure 15:
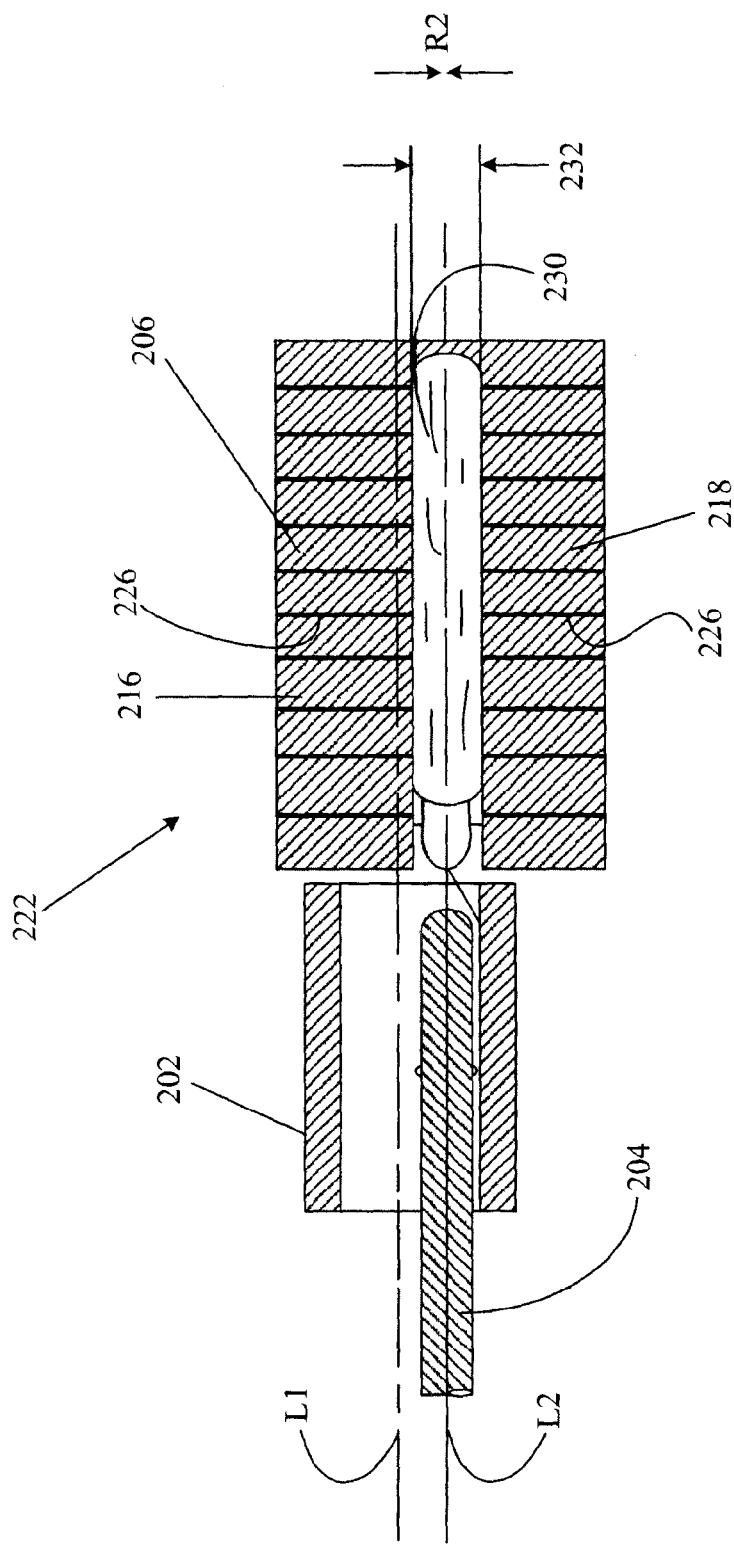
FIG. 15 is a cross-sectional view of an embodiment of the invention showing a pledget being compressed into a compressed pledget in the compression mold.

FIG. 15 is a cross-sectional view of an embodiment of the invention showing pledget 210 being compressed into a compressed pledget 230 in the compression/stabilization mold 206 when the compression/stabilization mold 206 is in the closed position 222. In the closed position 222, the compression/stabilization mold 206 has an inside dimension 232 that can be any dimension suitable for compressing the pledget 210 into a desired compressed dimension. For example, in one embodiment of the invention, the inside dimension 232 is compressed to about 12.5 mm. The pledget 210 may be partially compressed in compression/stabilization mold 206, thereby forming the compressed pledget 230.

Figure 16:
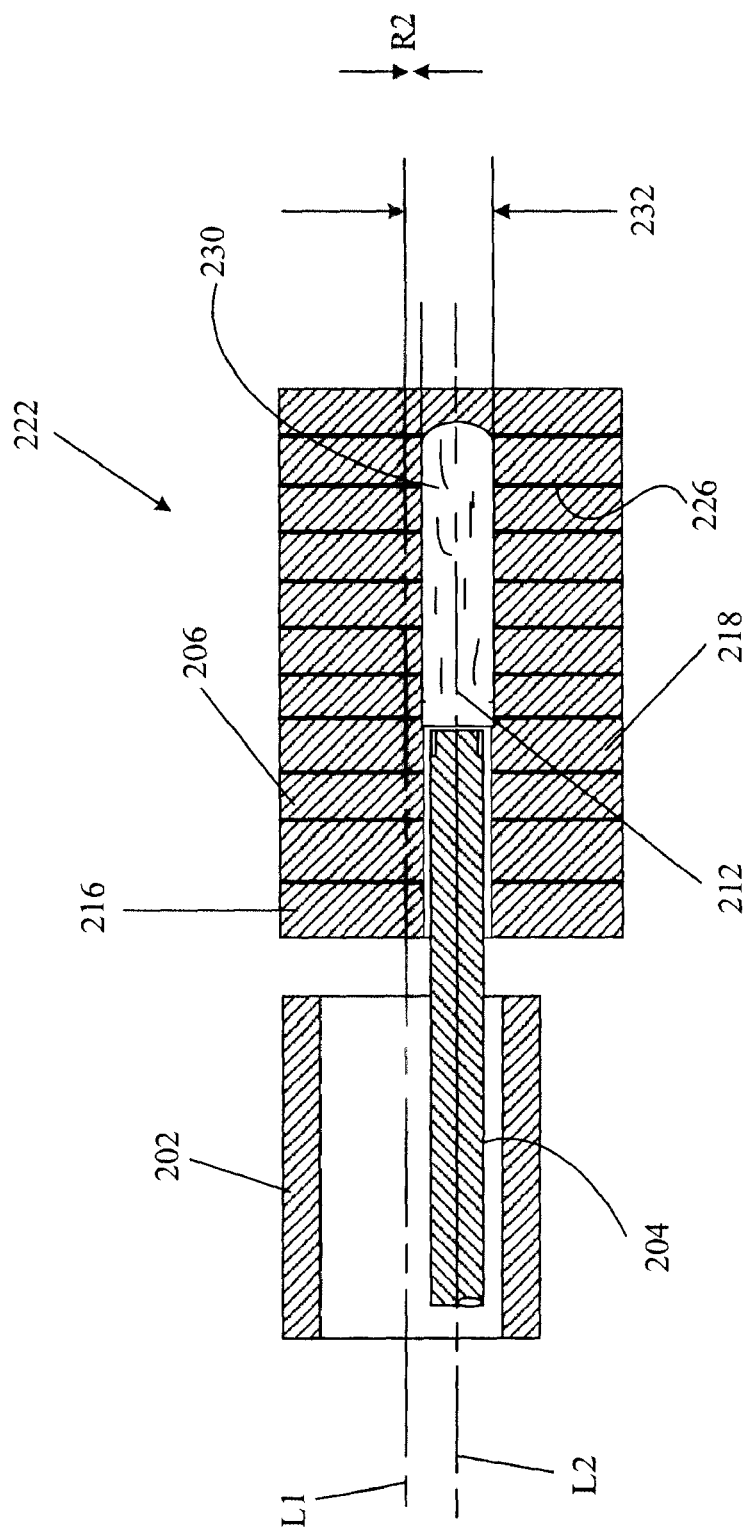
FIG. 16 is a cross-sectional view of one embodiment of the transfer member further compressing the compressed pledget in the compression mold.

In certain embodiments, such as shown in FIG. 16, the compressed pledget 230 can be further compressed or compacted when the transfer member 204 applies a force to one end of the compressed pledget 230, thereby pressing an opposing end further into the compression/stabilization mold 206.

In certain embodiments, at least one header for forming a patterned impression in at least one end of the compressed pledget, such as 230, can be used. In these embodiments, for example, the transfer member 204 may be used to impart a force on one end of the compressed pledget 230 such that the opposing end may contact the at least one header to form a patterned impression in an end of the compressed pledget 230. In another example, at least one header may be moved to contact at least one end of the compressed pledget 230 to form a patterned impression in an end of the compressed pledget 230. Examples of headers and suitable equipment for forming patterned impressions in at least one end of a compressed pledget are disclosed in U.S. patent application Ser. No. 11/799,914, filed May 3, 2007, entitled "Tampon with Patterned End and Method and Apparatus for Making Same".

The closed position 222 may be accomplished by moving the first compression mold member 216 in the direction R2 toward the second compression mold member 218. However, as noted above, other contemplated embodiments of the invention can include both moving mold members or multiple moving mold members. During the closing of the compression/stabilization mold 206, the pledget 210 undergoes a radial or lateral compression in the direction R2, reducing the radial or lateral dimension of the pledget to approximately the inside dimension 232, which may be any suitable dimension, for example, about 12.5 mm. Thus, in one example, the first compression mold member 216 moved radially or laterally from about 40.5 mm to about 12.5 mm, resulting in a total movement of about 28 mm.

In certain embodiments, the transfer member 204 can also move to become aligned along a second longitudinal centerline L2 aligned with the closed position 222 of the compression/stabilization mold 206. The distance between the first longitudinal centerline L1 and the second longitudinal centerline L2 can be approximately dimension 232, which may be about half of the radial or lateral movement of the first compression mold member 216. For example, in the particular example above, when the first compression mold member 216 moves about 28 mm, the transfer member 204 can move the approximate distance 232 of about 14 mm.

According to certain embodiments, the compressed pledget 104 may be heated in the compression/stabilization mold 206 to impart a self-sustaining shape to the compressed pledget 230 and resulting tampon. Methods of setting or stabilizing the tampon shape include heating the compressed pledget 104 with steam as disclosed in U.S. patent application Ser. No. 10/887,645 or thermal temperature gradient conduction or microwaving, as disclosed in U.S. Pat. No. 7,047,608. Various methods involving heat conduction, radiant heat, and microwaves can be used in accordance with various embodiments of the invention.

In certain embodiments, a heated gas or other medium can be applied to the compressed pledget 230 via the at least one pore 226 while the compressed pledget 230 is within the closed compression/stabilization mold 206. Methods of setting or stabilizing the tampon shape in this manner are disclosed in U.S. patent application Ser. No. 10/887,645, filed Jul. 9, 2004, entitled "Compressed, Gas-Stabilized Tampon Having Multiple Folds;" U.S. patent application Ser. No. 11/595,322, filed Nov. 10, 2006, entitled "System and Method for an Expandable Pushrod Mold Seal;" and U.S. patent application Ser. No. 11/601,946, filed Nov. 20, 2006, entitled "Method and Apparatus for Producing Stabilized Absorbent Article".

Figure 17:
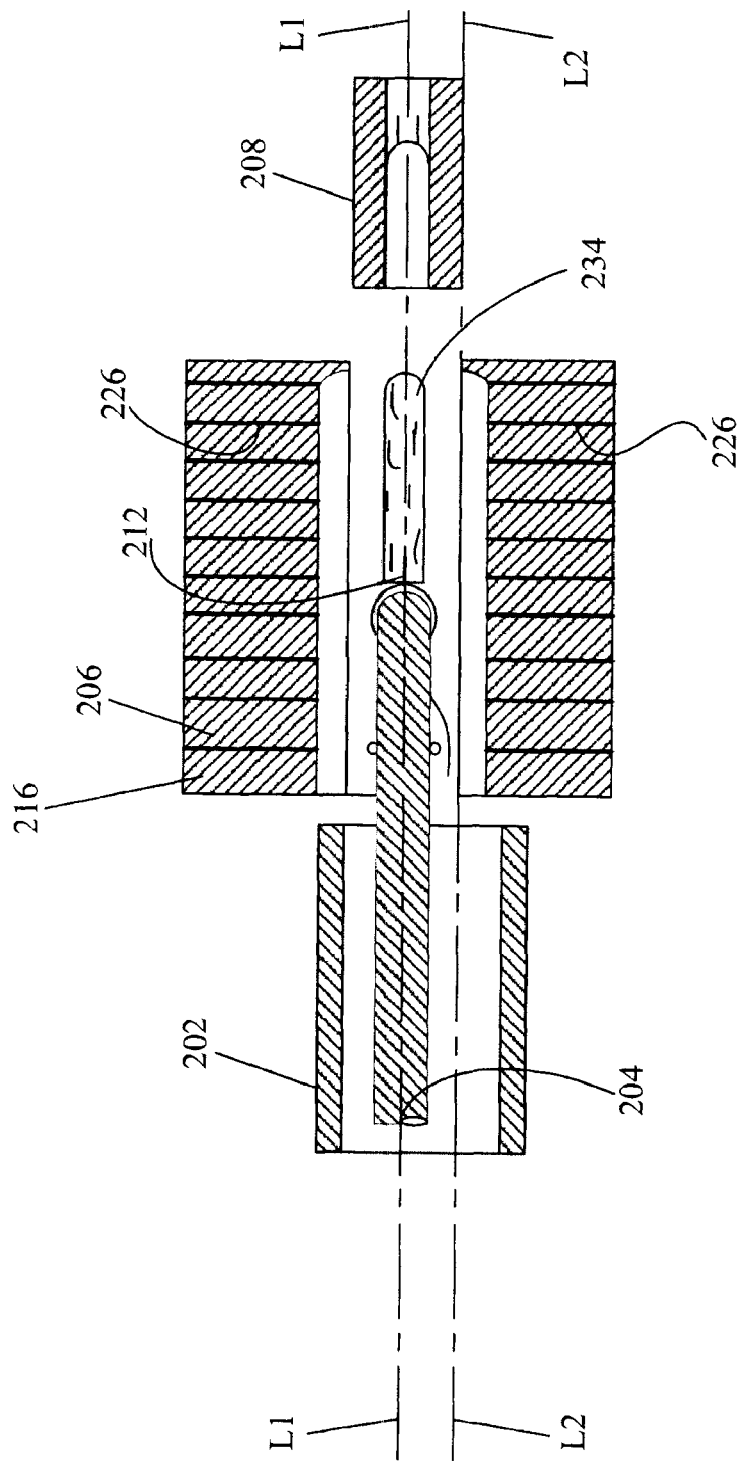
FIG. 17 is a cross-sectional view of an embodiment of the invention showing the opening of the compression mold for removal of the formed tampon.

FIG. 17 is a cross-sectional view of an embodiment of the invention showing a resulting or formed tampon 234 being removed from the compression/stabilization mold 206. In this embodiment, the compression/stabilization mold 206 can be opened by moving the first member 216 of the compression/stabilization mold 206 in the direction R1. However, as was noted above with respect to the compression/stabilization mold 206, the compression/stabilization mold 206 can also include two or more moving mold members.

The transfer member 204 may load the resulting or formed tampon 234 into the product discharge carrier 208 with a controlled loading stroke that is followed by a controlled transfer member 204 retraction after stabilizing the compressed pledget 132 in the compression/stabilization mold 206.

Figure 18:
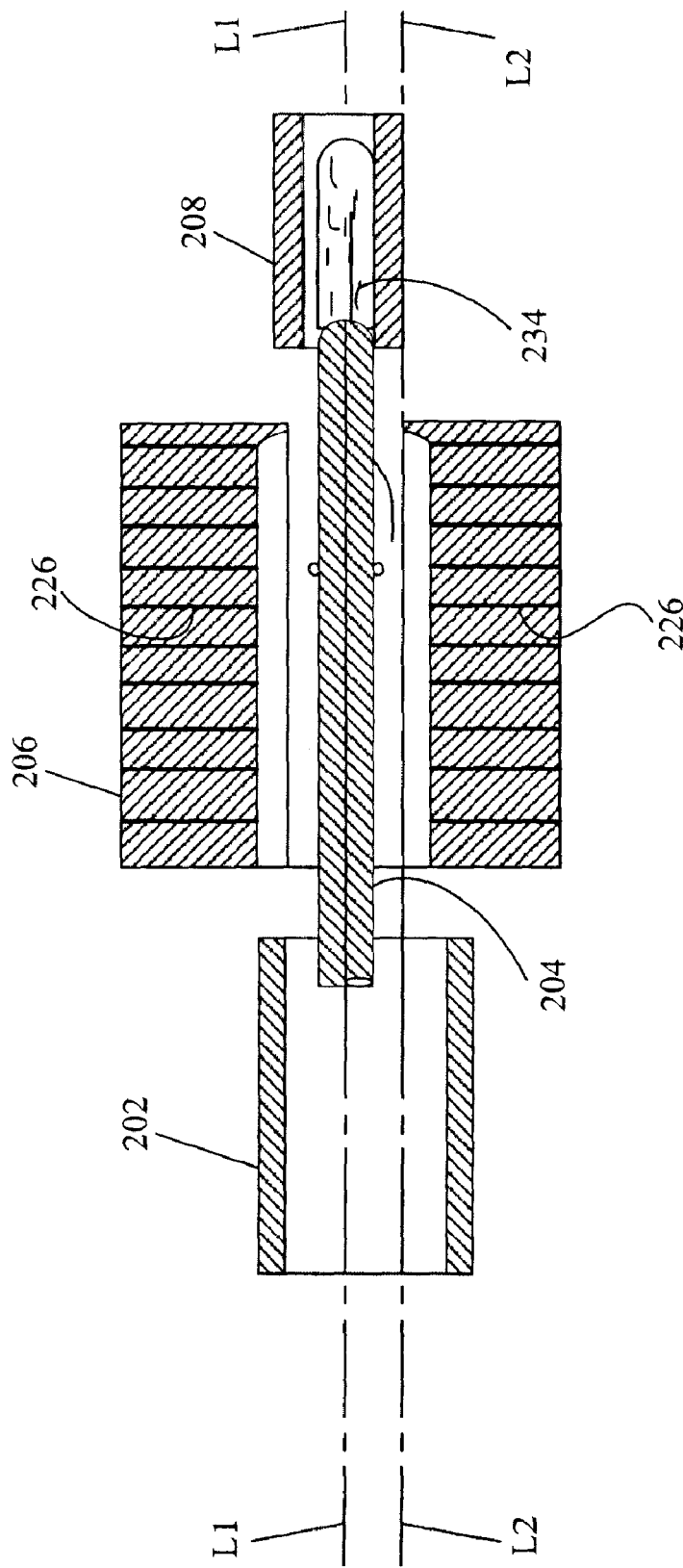
FIG. 18 is a cross-sectional view of an embodiment of the invention showing the removal of the formed tampon from the compression mold.

FIG. 18 is a cross-sectional view of one embodiment of the transfer member 204 loading the resulting or formed tampon 234 into the product discharge carrier 208 when the transfer member 204 has completed the loading stroke.

Figure 19:
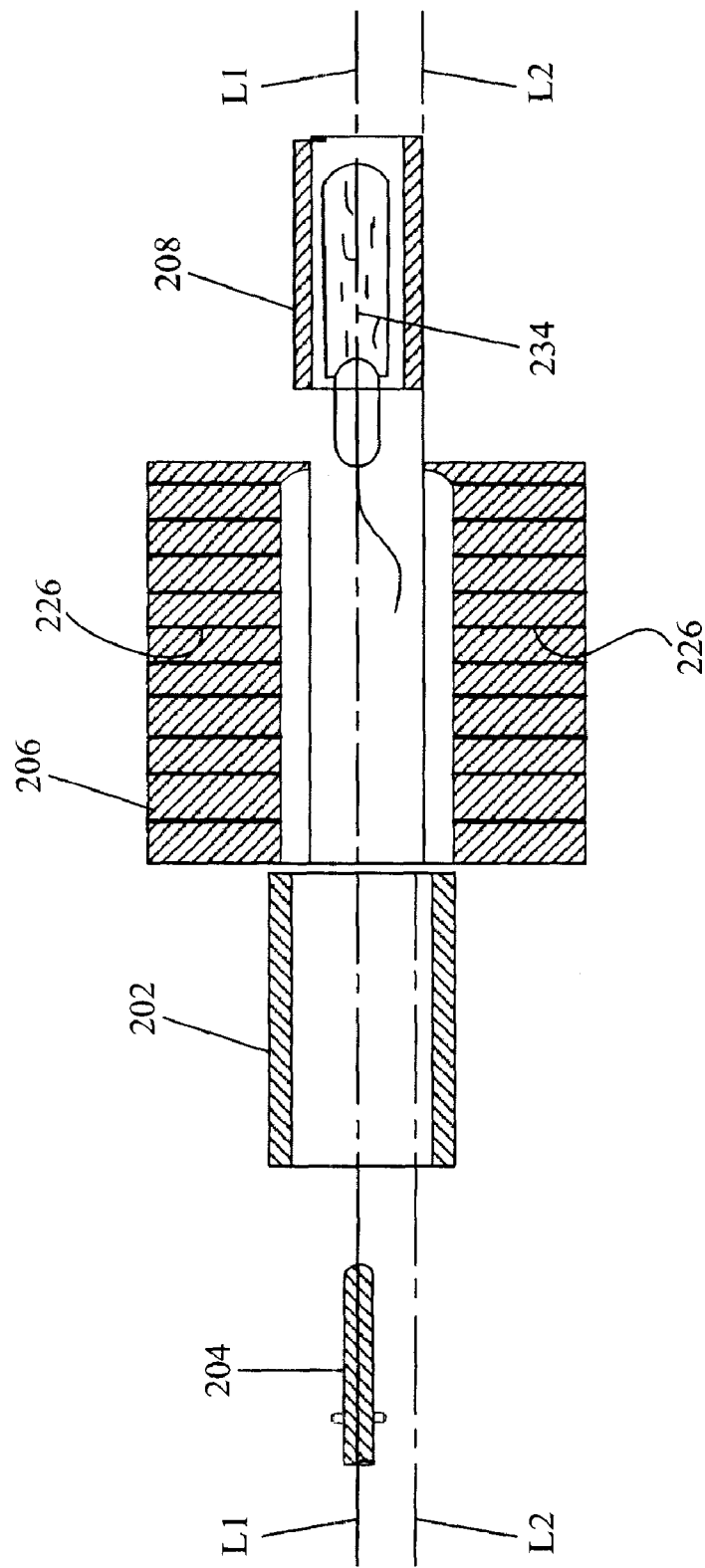
FIG. 19 is a cross-sectional view of an embodiment of the invention showing the removal of the formed tampon from the compression mold.

FIG. 19 is a cross-sectional view of the retraction of the transfer member 204 from the formed tampon 230 leaving the resulting or formed tampon 234 adjacent to the product discharge carrier 208.

The tampon forming apparatus described in FIGS. 2-19 is shown by way of example. Other tampon forming apparatus may have similar or other components and configurations in accordance with other embodiments of the invention.

C. Method of Making Tampons

Figure 6:
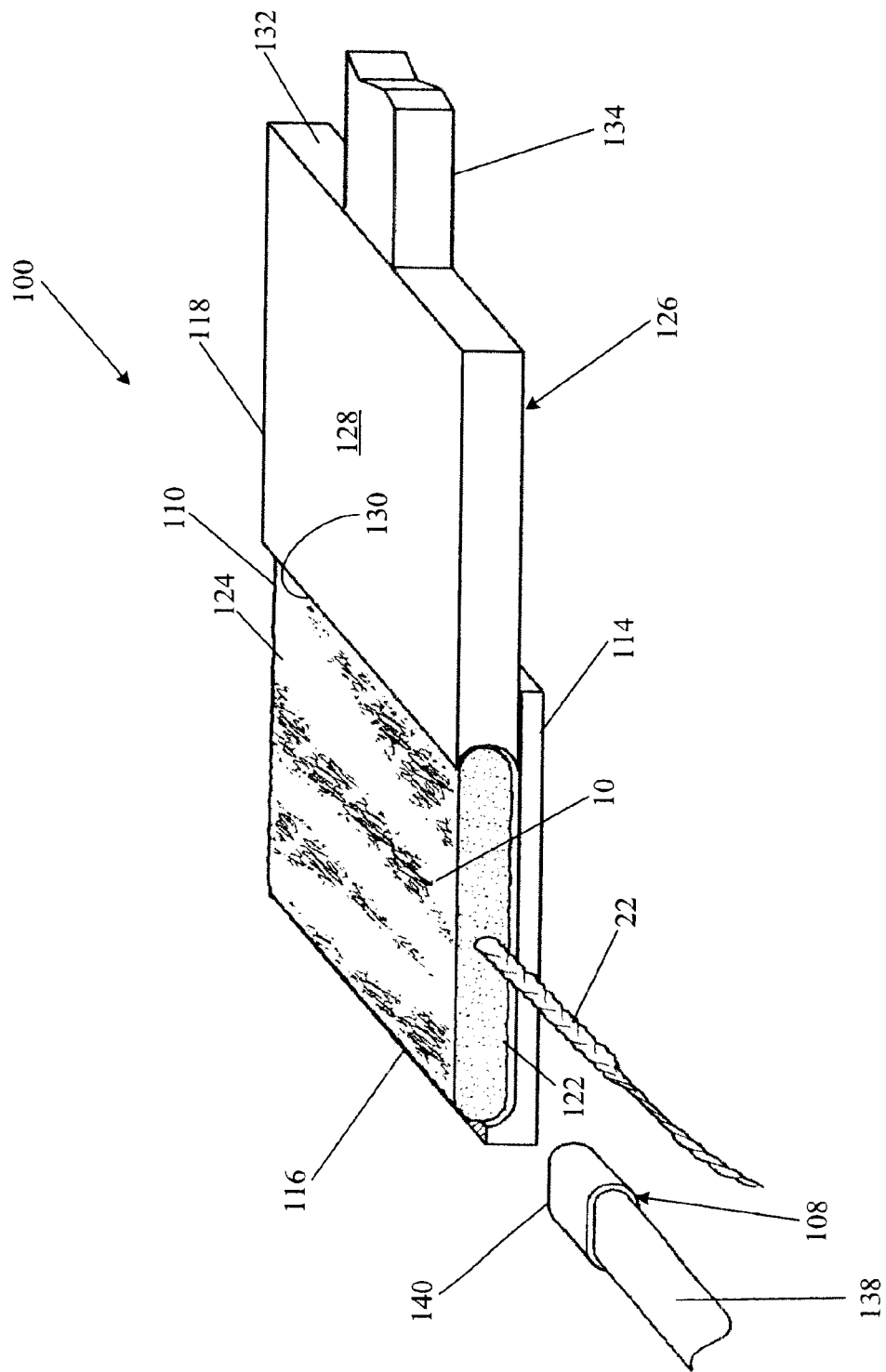
FIG. 6 is partial perspective view of the tampon forming apparatus in FIG. 2 with the tampon compression crossdie in open position and an uncompressed pledget in the tampon compression machine cavity.

A tampon, for instance 300 in FIG. 20, may be made in accordance with an embodiment of this invention by inserting the uncompressed pledget 10 in the open compression machine cavity 136 as shown in FIG. 6, compressing the pledget 10 by closing the compression machine cavity 136, and stabilizing the compressed pledget while the compressed pledget is within the compression machine cavity 136.

As described hereinbefore, the thickness T1 of the uncompressed pledget 10 may be very close to the thickness T2 of the compression machine cavity 136 and the width W1 of the uncompressed pledget 10 may be close to or less than the width W2 of the compression machine cavity 136. The length L1 of the uncompressed pledget 10, however, may be less than the length L2 of the compression machine cavity 136. According to certain embodiments, the thickness of the uncompressed pledget 10 can vary as can the particular dimensions of the compression machine cavity 136, and compression member head 140, but, according to certain embodiments, uncompressed pledget 10 thickness may generally range from about 5 mm to about 15 mm, or from about 5 mm to about 12 mm, or from about 5 mm to about 9.8 mm.

Figure 7:
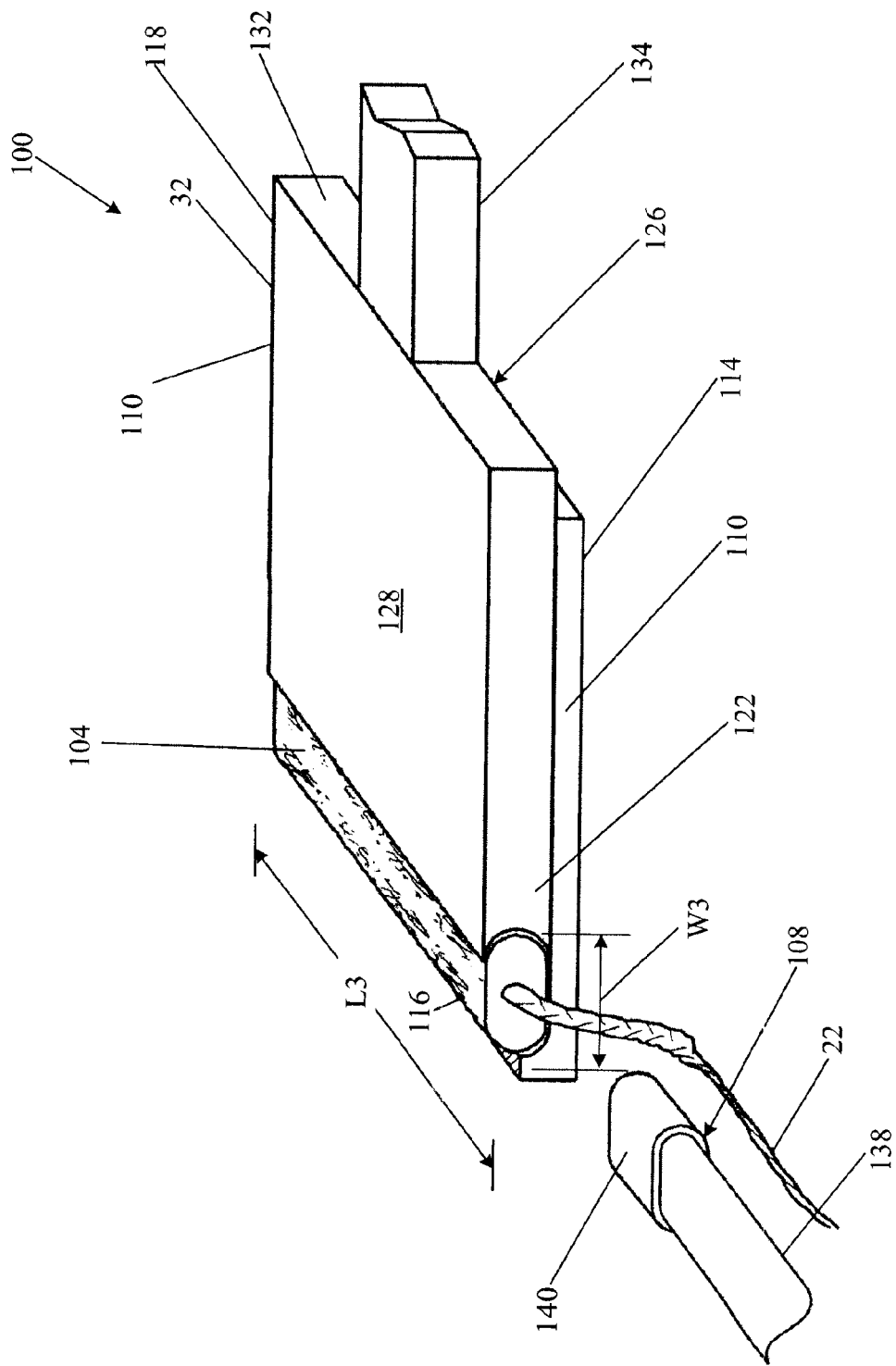
FIG. 7 is partial perspective view of the tampon forming apparatus in FIG. 2 with the tampon compression crossdie in a final compression position and a compressed pledget in the tampon compression machine cavity.

After an uncompressed pledget 10 is inserted within the open compression machine cavity 136 as shown in FIG. 6, the uncompressed pledget 10 may be compressed in the compression machine cavity 136 by actuating the die or force application member 126 of a tampon compression crossdie 102 within the anvil channel 120 toward the end wall 116 of the anvil 110 until the compressed configuration illustrated in FIGS. 4 and 7 is reached. The amount of force required to compress the pledget 10 may vary but suitable forces typically are from about 40 psi to about 300 psi. A variety of techniques for actuating the compression die or force application member 126 are well known and may include, but are not limited to a modified tampon compression crossdie available from Tory Engineering Company, of Osaka, Japan. According to certain embodiments, the compressed pledget width W3 is predetermined and the compression crossdie 102 compresses the uncompressed pledget 10 only to the compressed pledget width W3. In accordance with certain embodiments, methods for stopping the compression applied by the die or force application member 126 may include, but are not limited to a stop or détente structure for stopping forward movement of the die or force application member 126 when the predetermined compressed pledget width W3 is reached or suitable controls on the actuating mechanism for reciprocating the die or force application member 126.

Figure 8:
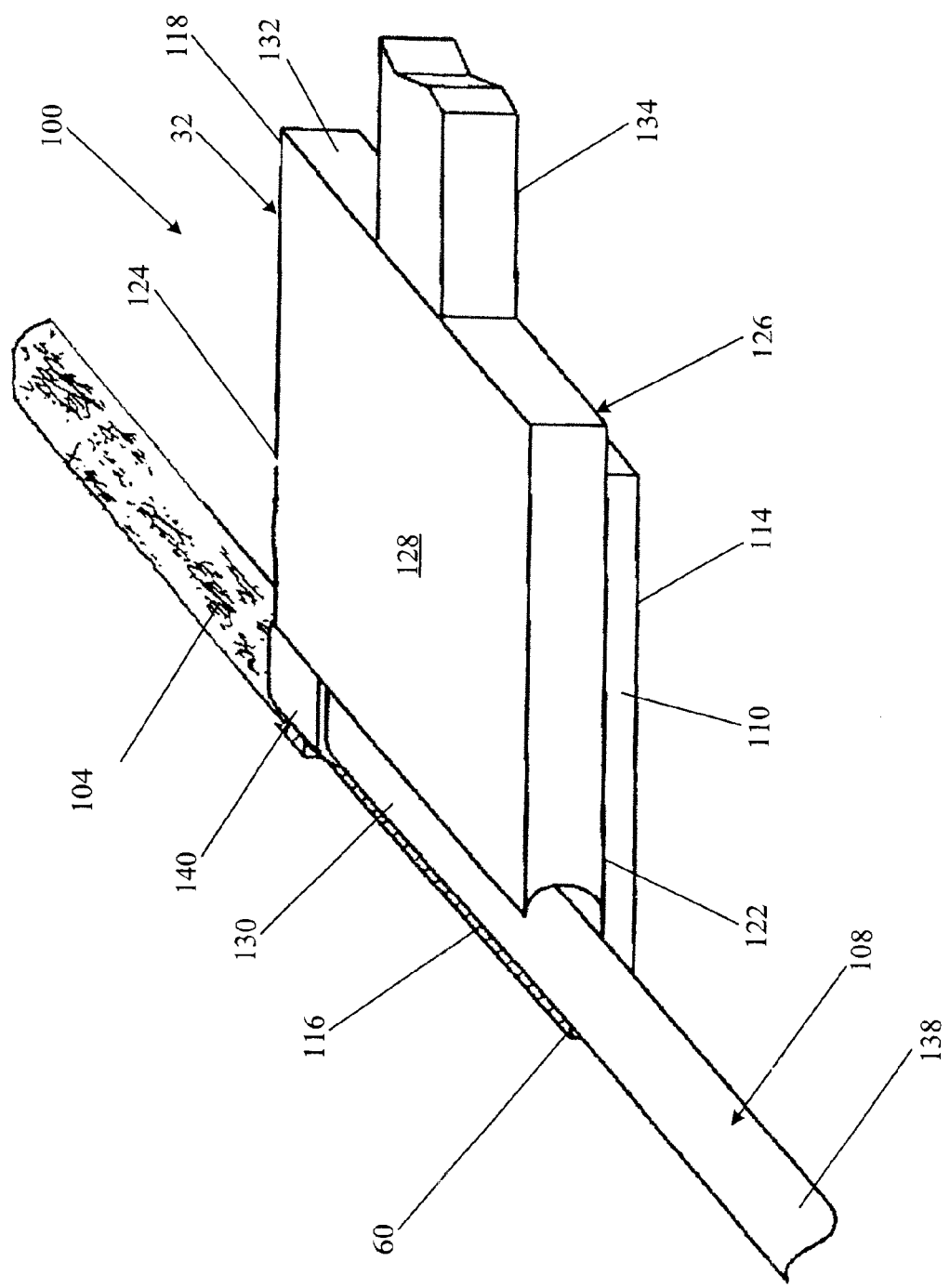
FIG. 8 is a partial perspective view of the tampon forming apparatus of FIG. 2 with a compressed pledget removed from the tampon compression machine cavity.

After compression in the tampon compression crossdie 102, the die or force application member 126 may retract and permit the compressed pledget 104 to be ejected from the compression machine cavity 136. In this embodiment, the transfer member 108 may be actuated so that the compression member head 140 enters the inlet end 122 of the compression machine cavity 136 and extends through the compression machine cavity 136, with the die or force application member 126 partially or fully retracted, thereby forcing the compressed pledget 104 out of the compression machine cavity 136 until the compressed pledget 104 is completely ejected or removed from the compression machine cavity 136 as shown in FIG. 8. The compressed pledget 104 may be further transferred or removed from the vicinity of the tampon compression crossdie 102 by conventional means such as by pulling the withdrawal cord 22, manually or mechanically by grasping, hooking, picking, or clamping the tampon and withdrawing it from the mold, or vacuum withdrawal, or the like. Suitable methods of tampon removal from a compression mold are described in U.S. Pat. No. 7,047,608.

A tampon, for instance 300 in FIG. 20, may be made in accordance with another embodiment of this invention by inserting an uncompressed pledget 10 in the open compression/stabilization mold 206 of the tampon forming apparatus 200 as shown in FIGS. 9-19. Similar to the method described above with respect to FIGS. 2-8, the tampon forming apparatus 200 may compress the pledget 10 by closing the compression/stabilization mold 206, and may stabilize the compressed pledget 230 while the compressed pledget 230 is within the closed compression/stabilization mold 206.

D. Tampons

Tampons made by the foregoing method may have a relatively smooth or patterned outer surface. Certain tampons may have a substantially consistent density profile along the body of the tampon. A tampon 300 made in accordance with an embodiment of this invention is illustrated in FIG. 20. The tampon 300 illustrated in FIG. 20 is made according to an embodiment of this invention. The body region and/or the head region may have a patterned impression comprising one or more design elements. Further, the tampon may be relatively smooth along the length and/or across the width of the surface of the tampon. In certain embodiments, a majority of such patterns penetrate no deeper than about 20% of the width of the tampon. In certain embodiments, all the patterns but a crease created by the withdrawal cord 302 penetrate no deeper than about 20% of the tampon width.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the invention. To the extent that any meaning or definition of a term in this document conflicts with any meaning or definition of the same term in a document incorporated by reference, the meaning or definition assigned to that term in this document shall govern.

While particular embodiments of the invention have been illustrated and described, it would be obvious to those skilled in the art that various other changes and modifications can be made without departing from the scope of the invention. It is therefore intended to cover in the appended claims all such changes and modifications that are within the scope of this invention.

What is claimed is:

1. A method for producing a stabilized tampon from a tampon pledget, the method comprising:
   providing a tampon pledget;
   providing a compression mold;
   moving the tampon pledget into the compression mold via a transfer member, wherein the compression mold is in an open position; and compressing the tampon pledget in the compression mold by closing the compression mold, wherein lateral compression of the tampon pledget is done in a single step;

forming a stabilized tampon within the compression mold.

2. The method of claim 1, further comprising:

applying at least one gas to the compressed tampon in the compression mold to facilitate forming a stabilized tampon.

3. The method of claim 1, further comprising:

applying heat to the compressed tampon in the compression mold to facilitate forming a stabilized tampon.

4. The method of claim 1, wherein the compression mold comprises at least one pattern structure capable of forming a corresponding pattern on the stabilized tampon.

5. The method of claim 1, wherein the compression mold comprises a plurality of fluid communication passages capable of receiving at least one gas to facilitate forming a stabilized tampon.

6. The method of claim 5, further comprising applying fluid pressure through said fluid communication passages to deform said tampon pledget into a pre-folded shape prior to compressing the tampon pledget in the compression mold.

7. The method of claim 1, further comprising:

laterally or axially compressing the tampon pledget when the tampon pledget is within the compression mold.

8. The method of claim 1, wherein the compression mold comprises a plurality of mold members, wherein at least some of the mold members are capable of compressing the tampon pledget in a lateral direction, and wherein at least some of the mold members are capable of compressing the tampon pledget in an axial direction.

9. The method of claim 7, wherein the compression mold comprises at least one pattern structure capable of forming a corresponding patterned impression on the stabilized tampon when the tampon pledget is axially compressed.

10. A method for producing a stabilized tampon from a tampon pledget, the method comprising:

providing a tampon pledget;

providing a compression mold;

moving the tampon pledget into the compression mold via a transfer member, wherein the compression mold is in an open position; and laterally compressing the tampon pledget in the compression mold by closing the compression mold, wherein lateral compression of the tampon pledget is done in a single step;

forming a stabilized tampon within the compression mold substantially in the absence of axial compression.

11. A method for producing a stabilized tampon from a tampon pledget, the method comprising:

providing a tampon pledget;

providing a compression mold;

moving the tampon pledget into the compression mold via a transfer member, wherein when the compression mold is in an open position the tampon pledget is circumferentially contained within a cavity of the compression mold; and compressing the tampon pledget in the compression mold by closing the compression mold so that the cavity is reduced in volume, wherein lateral compression of the tampon pledget is done in a single step;

thereby forming a stabilized tampon within the compression mold.

* * * * *